(12) United States Patent
Nakamura et al.

(10) Patent No.: US 10,980,858 B2
(45) Date of Patent: Apr. 20, 2021

(54) TROPHIC FACTOR RELEASING AGENT AND INFLAMMATORY DISEASE TREATING AGENT

(71) Applicant: FUJIFILM Corporation, Tokyo (JP)

(72) Inventors: Kentaro Nakamura, Kanagawa (JP); Sayako Kozakai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 31 days.

(21) Appl. No.: 16/226,348

(22) Filed: Dec. 19, 2018

(65) Prior Publication Data

US 2019/0192632 A1 Jun. 27, 2019

Related U.S. Application Data

(63) Continuation of application No. PCT/JP2017/022500, filed on Jun. 19, 2017.

(30) Foreign Application Priority Data

Jun. 20, 2016 (JP) .............................. JP2016-121867
Oct. 12, 2016 (JP) .............................. JP2016-200629
May 24, 2017 (JP) .............................. JP2017-102525

(51) Int. Cl.
| | |
|---|---|
| *A61P 29/00* | (2006.01) |
| *A61K 38/19* | (2006.01) |
| *A61K 35/28* | (2015.01) |
| *A61P 1/00* | (2006.01) |
| *A61K 47/36* | (2006.01) |
| *A61K 47/42* | (2017.01) |
| *C07K 14/78* | (2006.01) |
| *A61K 41/17* | (2020.01) |
| *A61K 47/60* | (2017.01) |
| *A61K 9/00* | (2006.01) |
| *A61K 9/107* | (2006.01) |
| *A61K 9/70* | (2006.01) |
| *A61K 38/01* | (2006.01) |
| *A61K 38/39* | (2006.01) |
| *A61K 47/34* | (2017.01) |

(52) U.S. Cl.
CPC ............ *A61K 38/19* (2013.01); *A61K 9/0002* (2013.01); *A61K 9/0024* (2013.01); *A61K 9/1075* (2013.01); *A61K 9/703* (2013.01); *A61K 35/28* (2013.01); *A61K 38/014* (2013.01); *A61K 38/39* (2013.01); *A61K 41/17* (2020.01); *A61K 47/34* (2013.01); *A61K 47/36* (2013.01); *A61K 47/42* (2013.01); *A61K 47/60* (2017.08); *A61P 1/00* (2018.01); *A61P 29/00* (2018.01); *C07K 14/78* (2013.01)

(58) Field of Classification Search
None
See application file for complete search history.

(56) References Cited

U.S. PATENT DOCUMENTS

| | | | |
|---|---|---|---|
| 9,211,266 B2 * | 12/2015 | Iwazawa | A61P 43/00 |
| 10,500,311 B2 * | 12/2019 | Nakamura | A61K 35/28 |
| 2005/0239897 A1 | 10/2005 | Pittenger et al. | |
| 2012/0329157 A1 | 12/2012 | Nakamura | |
| 2017/0095595 A1 | 4/2017 | Nakamura | |

FOREIGN PATENT DOCUMENTS

| | | | | |
|---|---|---|---|---|
| EP | 2543397 A1 | 1/2013 | | |
| EP | 2564880 A1 * | 3/2013 | | A61L 27/22 |
| JP | 2007-530543 A | 11/2007 | | |
| JP | 2009-7321 A | 1/2009 | | |
| JP | 4819356 B2 | 11/2011 | | |
| JP | 2015-134193 A | 7/2015 | | |
| WO | WO 2011/108517 A1 | 9/2011 | | |
| WO | WO 2015/194494 A1 | 12/2015 | | |

OTHER PUBLICATIONS

Ylostalo, Stem Cells 2012;30:2283-2296 (Year: 2012).*
Hayashi, Acta Biomaterialia 7 (2011) 2797-2803 (Year: 2011).*
Milner, Journal of Cell Science, 2003, 116, 1863-1873 (Year: 2003).*
Extended European Search Report, dated May 27, 2019, for corresponding European Application No. 17815347.4.
Hayashi et al., "Preparation of Stem Cell Aggregates with Gelatin Microspheres to Enhance Biological Functions," Acta Biomaterialia, vol. 7, No. 7, Available online Apr. 20, 2011 (Apr. 13, 2011), pp. 2797-2803, XP028095824.
Iwazawa et al., "The Therapeutic Effects of Adipose-Derived Stem Cells and Recombinant Peptide Pieces on Mouse Model of DSS Colitis," Cell Transplantation, vol. 27, No. 9, 2018 (Sep. 2018), pp. 1390-1400, XP55588828.
Nakamura et al., "Introduction to a New Cell Transplantation Platform via Recombinant Peptide Petaloid Pieces and Its Application to Islet Transplantation with Mesenchymal Stem Cells," Transplant International, vol. 29, No. 9, 2016 (Jun. 16, 2016), pp. 1039-1050, XP055587752.
Xiang et al., "Bone Marrow Mesenchymal Stem Cells in a Three-Dimensional Gelatin Sponge Scaffold Attenuate Inflammation, Promote Angiogenesis, and Reduce Cavity Formation in Experimental Spinal Cord Injury," Cell Transplantation, vol. 20, No. 11-12, pp. 1881-1899, XP55588832.

(Continued)

*Primary Examiner* — Satyanarayana R Gudibande
(74) *Attorney, Agent, or Firm* — Birch, Stewart, Kolasch & Birch, LLP.

(57) ABSTRACT

An object of the present invention is to provide a trophic factor releasing agent and an inflammatory disease treating agent in which an amount of trophic factors released from cells in a cell transplantation treatment or the like is increased. According to the present invention, there is provided a trophic factor releasing agent including a cell structure that includes biocompatible polymer blocks and cells and in which a plurality of the biocompatible polymer blocks are disposed in gaps between a plurality of the cells, in which a size of one of the biocompatible polymer blocks is 20 μm to 200 μm, and trophic factors are released from the cells.

15 Claims, 12 Drawing Sheets

Specification includes a Sequence Listing.

(56) References Cited

OTHER PUBLICATIONS

Japanese Office Action dated Feb. 4, 2020, for corresponding Japanese Patent Application No. 2018-524075, with English translation.
Bartosh et al., "Aggregation of Human Mesenchymal Stromal Cells (MSCs) into 3D Spheroids Enhances Their Antiinflammatory Properties", PNAS, vol. 107, No. 31, Aug. 3, 2010, pp. 13724-13729.
Chen et al., "Gene Delivery with IFN-γ-Expression Plasmids Enhances the Therapeutic Effects of MSCs on DSS-Induced Mouse Colitis", Inflammation Research, vol. 64, Published online Jul. 8, 2015, pp. 671-681.
Grégoire et al., "Review Article: Mesenchymal Stromal Cell Therapy for Inflammatory Bowel Diseases", Aliment Pharmacol Ther, vol. 45, Published online Nov. 22, 2016, pp. 205-221.
Honmou, "A Cell Therpay for Stroke", Clinical Evaluation, vol. 36, Supplemental XXVI, Jul. 10, 2009, pp. 132-139 (10 pages total).
International Preliminary Report on Patentability and Written Opinion of the International Searching Authority (Forms PCT/IB/326, PCT/IB/373 and PCT/ISA/237) for International Application No. PCT/JP2017/022500, dated Jan. 3, 2019, with English translation of the Written Opinion.
International Search Report (form PCT/ISA/210) for International Application No. PCT/JP2017/022500 dated Aug. 8, 2017, with English Translation.
Ylö stalo et al., "Human Mesenchymal Stem/Stromal Cells Cultured as Spheroids Are Self-Activated to Produce Prostaglandin E2 That Directs Stimulated Macrophages Into an Anti-Inflammatory Phenotype", Stem Cells, vol. 30, Published online Aug. 3, 2012, pp. 2283-2296 (15 pages total).
European Office Action dated Jul. 16, 2020 for Application No. 17 815 347.4.
Japanese Office Action for Japanese Application No. 2018-524075, dated Aug. 13, 2019, with English translation.
OSAMU, "A cell therapy for stroke," Medical Evaluation, vol. 36, Suppl XXVI, 2009, pp. 132-139.

* cited by examiner

FIG. 1
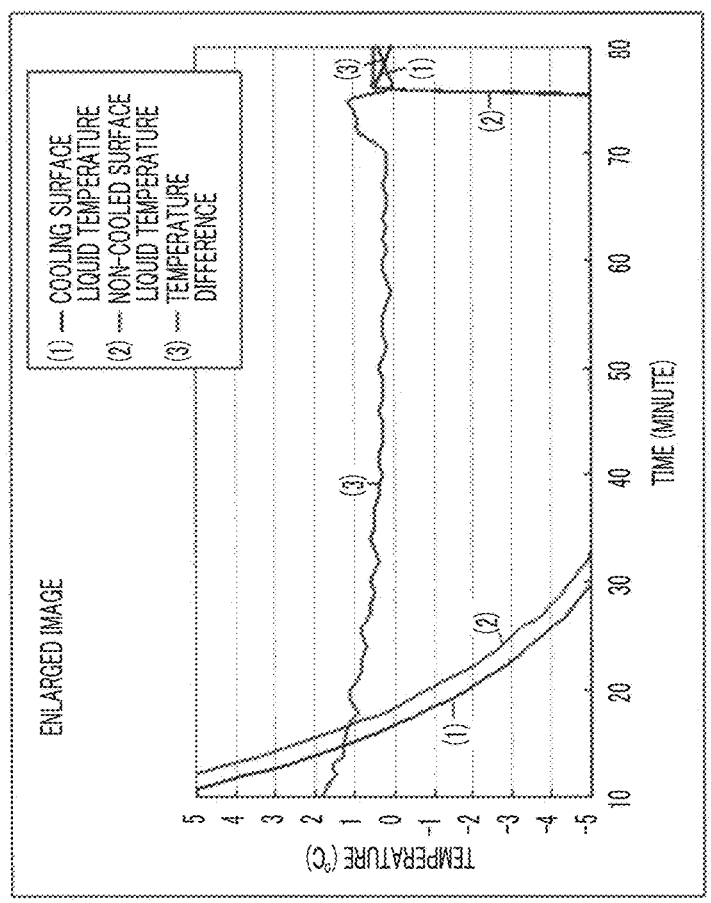
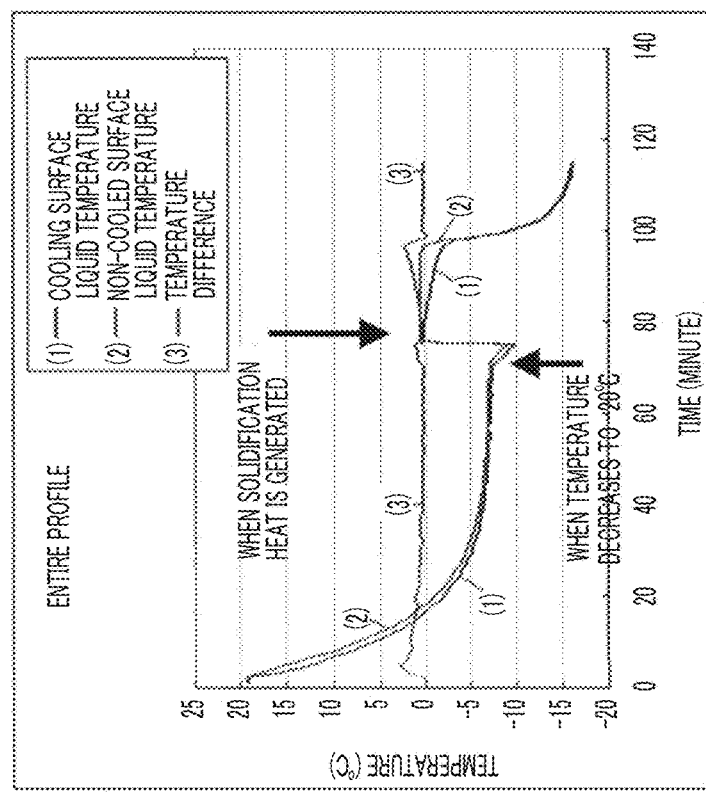

FIG. 2
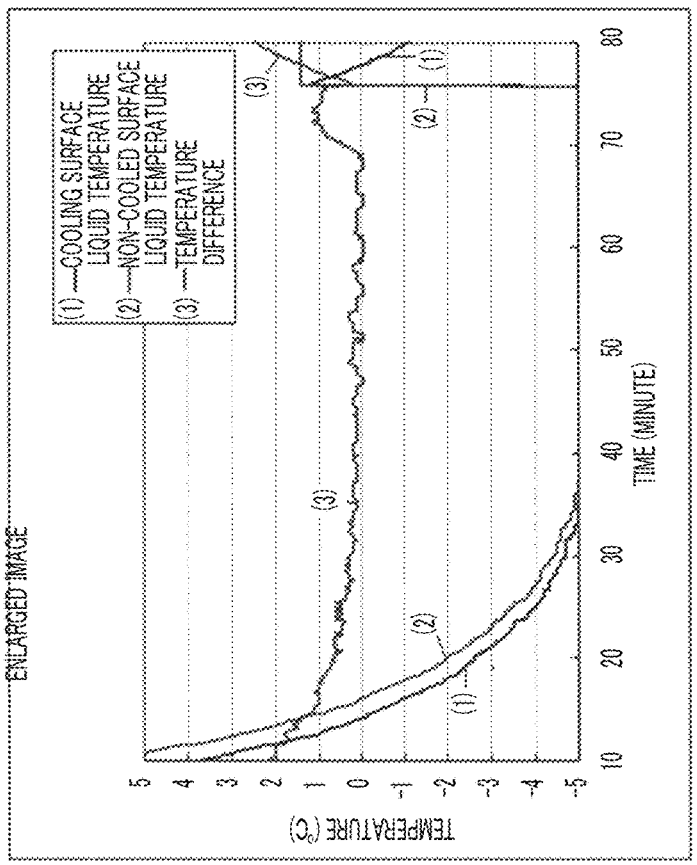
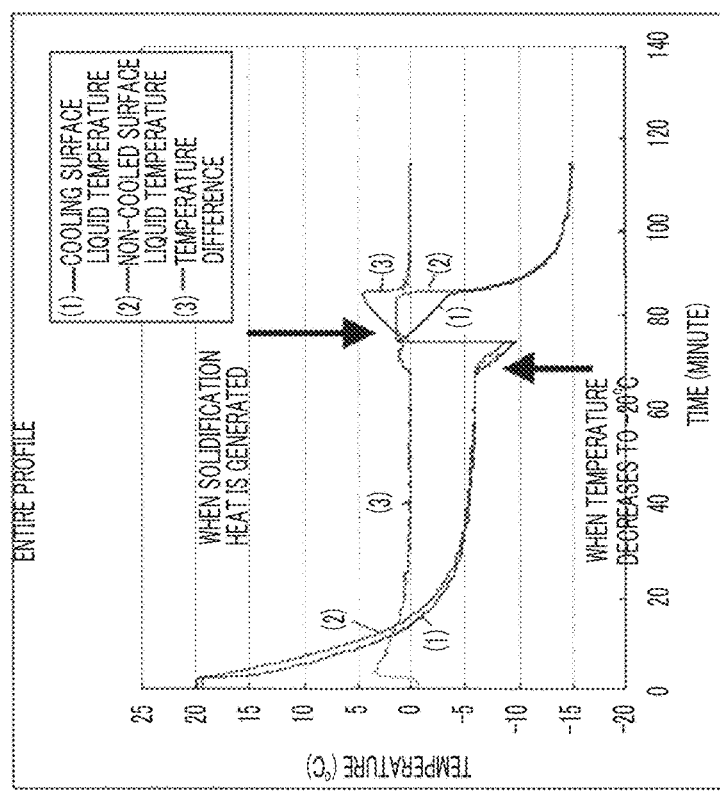

SEQUENCE LISTING

```
<160> NUMBER OF SEQ ID NOS: 11

<210> SEQ ID NO 1
<211> LENGTH: 571
<212> TYPE: PRT
<213> ORGANISM: Artificial Sequence
<220> FEATURE:
<223> OTHER INFORMATION: Description of Artificial Sequence: Recombinant
      peptide

<400> SEQUENCE: 1

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
        115                 120                 125

Arg Gly Leu Ala Gly Pro Ile Gly Pro Pro Gly Pro Ala Gly Ala Pro
    130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
                165                 170                 175

Asp Gly Ala Pro Gly Lys Asp Gly Val Arg Gly Leu Ala Gly Pro Pro
            180                 185                 190
```

Gly Ala Pro Gly Leu Gln Gly Ala Pro Gly Leu Gln Gly Met Pro Gly
        195                 200                 205

Glu Arg Gly Ala Ala Gly Leu Pro Gly Pro Lys Gly Glu Arg Gly Asp
    210                 215                 220

Ala Gly Pro Lys Gly Ala Asp Gly Ala Pro Gly Ala Pro Gly Leu Gln
225                 230                 235                 240

Gly Met Pro Gly Glu Arg Gly Ala Ala Gly Leu Pro Gly Pro Lys Gly
            245                 250                 255

Glu Arg Gly Asp Ala Gly Pro Lys Gly Ala Asp Gly Ala Pro Gly Lys
        260                 265                 270

Asp Gly Val Arg Gly Leu Ala Gly Pro Ile Gly Pro Pro Gly Glu Arg
            275                 280                 285

Gly Ala Ala Gly Leu Pro Gly Pro Lys Gly Glu Arg Gly Asp Ala Gly
        290                 295                 300

Pro Lys Gly Ala Asp Gly Ala Pro Gly Lys Asp Gly Val Arg Gly Leu
305                 310                 315                 320

Ala Gly Pro Ile Gly Pro Pro Gly Pro Ala Gly Ala Pro Gly Ala Pro
            325                 330                 335

Gly Leu Gln Gly Met Pro Gly Glu Arg Gly Ala Ala Gly Leu Pro Gly
        340                 345                 350

Pro Lys Gly Glu Arg Gly Asp Ala Gly Pro Lys Gly Ala Asp Gly Ala
        355                 360                 365

Pro Gly Lys Asp Gly Val Arg Gly Leu Ala Gly Pro Pro Gly Ala Pro
        370                 375                 380

Gly Leu Gln Gly Ala Pro Gly Leu Gln Gly Met Pro Gly Glu Arg Gly
385                 390                 395                 400

Ala Ala Gly Leu Pro Gly Pro Lys Gly Glu Arg Gly Asp Ala Gly Pro
            405                 410                 415

Lys Gly Ala Asp Gly Ala Pro Gly Ala Pro Gly Leu Gln Gly Met Pro
        420                 425                 430

Gly Glu Arg Gly Ala Ala Gly Leu Pro Gly Pro Lys Gly Glu Arg Gly
        435                 440                 445

Asp Ala Gly Pro Lys Gly Ala Asp Gly Ala Pro Gly Lys Asp Gly Val
        450                 455                 460

Arg Gly Leu Ala Gly Pro Ile Gly Pro Pro Gly Glu Arg Gly Ala Ala
465                 470                 475                 480

Gly Leu Pro Gly Pro Lys Gly Glu Arg Gly Asp Ala Gly Pro Lys Gly
            485                 490                 495

Ala Asp Gly Ala Pro Gly Lys Asp Gly Val Arg Gly Leu Ala Gly Pro
            500                 505                 510

Ile Gly Pro Pro Gly Pro Ala Gly Ala Pro Gly Ala Pro Gly Leu Gln
        515                 520                 525

Gly Met Pro Gly Glu Arg Gly Ala Ala Gly Leu Pro Gly Pro Lys Gly
        530                 535                 540

Glu Arg Gly Asp Ala Gly Pro Lys Gly Ala Asp Gly Ala Pro Gly Lys
545                 550                 555                 560

Asp Gly Val Arg Gly Leu Ala Gly Pro Pro Gly
            565                 570

<210> SEQ ID NO 2
<211> LENGTH: 4
<212> TYPE: PRT
<213> ORGANISM: Artificial Sequence
<220> FEATURE:

-continued

```
<223> OTHER INFORMATION: Description of Artificial Sequence: Cell
      adhesion signal

<400> SEQUENCE: 2

Arg Glu Asp Val
1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 3

Tyr Ile Gly Ser Arg
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 4

Pro Asp Ser Gly Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 5

Arg Tyr Val Val Leu Pro Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 6

Leu Gly Thr Ile Pro Gly
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 7

Arg Asn Ile Ala Glu Ile Ile Lys Asp Ile
1               5                   10
```

```
<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 8

Ile Lys Val Ala Val
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 9

Asp Gly Glu Ala
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Cell
      adhesion signal

<400> SEQUENCE: 10

Glu Arg Gly Asp
1

<210> SEQ ID NO 11
<211> LENGTH: 571
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(571)
<223> OTHER INFORMATION: Every Xaa can be any naturally occurring amino
      acid

<400> SEQUENCE: 11

Gly Ala Pro Gly Xaa Xaa Gly Xaa Xaa Gly Xaa Xaa Gly Xaa Xaa Gly
1               5                   10                  15

Xaa Xaa Gly Xaa Xaa Gly Xaa Xaa Gly Xaa Xaa Gly Xaa Xaa Gly Xaa
                20                  25                  30

Xaa Gly Xaa Xaa Gly Xaa Xaa Gly Xaa Xaa Gly Xaa Xaa Gly Xaa Xaa
            35                  40                  45

Gly Xaa Xaa Gly Xaa Xaa Gly Xaa Xaa Gly Xaa Xaa Gly Xaa Xaa Gly
        50                  55                  60

Xaa Xaa Gly Xaa Xaa Gly Xaa Xaa Gly Xaa Xaa Gly Xaa Xaa Gly Xaa
65                  70                  75                  80

Xaa Gly Xaa Xaa Gly Xaa Xaa Gly Xaa Xaa Gly Xaa Xaa Gly Xaa Xaa
                85                  90                  95

Gly Xaa Xaa Gly Xaa Xaa Gly Xaa Xaa Gly Xaa Xaa Gly Xaa Xaa Gly
            100                 105                 110

Xaa Xaa Gly Xaa Xaa Gly Xaa Xaa Gly Xaa Xaa Gly Xaa Xaa Gly Xaa
        115                 120                 125
```

Xaa Gly Xaa Xaa Gly Xaa Xaa Gly Xaa Xaa Gly Xaa Xaa
    130                 135                 140

Gly Xaa Xaa Gly Xaa Xaa Gly Xaa Xaa Gly Xaa Xaa Gly
145                 150                 155                 160

Xaa Xaa Gly Xaa Xaa Gly Xaa Xaa Gly Xaa Xaa Gly Xaa
            165                 170                 175

Xaa Gly Xaa Xaa Gly Xaa Xaa Gly Xaa Xaa Gly Xaa Xaa
        180                 185                 190

Gly Xaa Xaa Gly Xaa Xaa Gly Xaa Xaa Gly Xaa Xaa Gly
    195                 200                 205

Xaa Xaa Gly Xaa Xaa Gly Xaa Xaa Gly Xaa Xaa Gly Xaa
    210                 215                 220

Xaa Gly Xaa Xaa Gly Xaa Xaa Gly Xaa Xaa Gly Xaa Xaa
225                 230                 235                 240

Gly Xaa Xaa Gly Xaa Xaa Gly Xaa Xaa Gly Xaa Xaa Gly
            245                 250                 255

Xaa Xaa Gly Xaa Xaa Gly Xaa Xaa Gly Xaa Xaa Gly Xaa
        260                 265                 270

Xaa Gly Xaa Xaa Gly Xaa Xaa Gly Xaa Xaa Gly Xaa Xaa
    275                 280                 285

Gly Xaa Xaa Gly Xaa Xaa Gly Xaa Xaa Gly Xaa Xaa Gly
290                 295                 300

Xaa Xaa Gly Xaa Xaa Gly Xaa Xaa Gly Xaa Xaa Gly Xaa
305                 310                 315                 320

Xaa Gly Xaa Xaa Gly Xaa Xaa Gly Xaa Xaa Gly Xaa Xaa
            325                 330                 335

Gly Xaa Xaa Gly Xaa Xaa Gly Xaa Xaa Gly Xaa Xaa Gly
        340                 345                 350

Xaa Xaa Gly Xaa Xaa Gly Xaa Xaa Gly Xaa Xaa Gly Xaa
    355                 360                 365

Xaa Gly Xaa Xaa Gly Xaa Xaa Gly Xaa Xaa Gly Xaa Xaa
    370                 375                 380

Gly Xaa Xaa Gly Xaa Xaa Gly Xaa Xaa Gly Xaa Xaa Gly
385                 390                 395                 400

Xaa Xaa Gly Xaa Xaa Gly Xaa Xaa Gly Xaa Xaa Gly Xaa
            405                 410                 415

Xaa Gly Xaa Xaa Gly Xaa Xaa Gly Xaa Xaa Gly Xaa Xaa
        420                 425                 430

Gly Xaa Xaa Gly Xaa Xaa Gly Xaa Xaa Gly Xaa Xaa Gly
    435                 440                 445

Xaa Xaa Gly Xaa Xaa Gly Xaa Xaa Gly Xaa Xaa Gly Xaa
    450                 455                 460

Xaa Gly Xaa Xaa Gly Xaa Xaa Gly Xaa Xaa Gly Xaa Xaa
465                 470                 475                 480

Gly Xaa Xaa Gly Xaa Xaa Gly Xaa Xaa Gly Xaa Xaa Gly
            485                 490                 495

Xaa Xaa Gly Xaa Xaa Gly Xaa Xaa Gly Xaa Xaa Gly Xaa
        500                 505                 510

Xaa Gly Xaa Xaa Gly Xaa Xaa Gly Xaa Xaa Gly Xaa Xaa
    515                 520                 525

Gly Xaa Xaa Gly Xaa Xaa Gly Xaa Xaa Gly Xaa Xaa Gly
530                 535                 540

```
Xaa Xaa Gly Xaa Xaa Gly Xaa Xaa Gly Xaa Xaa Gly Xaa Xaa Gly Xaa
545                 550                 555                 560

Xaa Gly Xaa Xaa Gly Xaa Xaa Gly Xaa Xaa Gly
            565                 570
```

TROPHIC FACTOR RELEASING AGENT AND INFLAMMATORY DISEASE TREATING AGENT

CROSS-REFERENCE TO RELATED APPLICATIONS

This application is a Continuation of PCT International Application No. PCT/JP2017/022500 filed on Jun. 19, 2017, which claims priority under 35 U.S.C § 119(a) to Japanese Patent Application No. 2016-121867 filed on Jun. 20, 2016, Japanese Patent Application No. 2016-200629 filed on Oct. 12, 2016 and Japanese Patent Application No. 2017-102525 filed on May 24, 2017. Each of the above application(s) is hereby expressly incorporated by reference, in its entirety, into the present application.

BACKGROUND OF THE INVENTION

1. Field of the Invention

The present invention relates to a trophic factor releasing agent and an inflammatory disease treating agent. Specifically, the present invention relates to a trophic factor releasing agent and an inflammatory disease treating agent including a cell structure that includes biocompatible polymer blocks and cells and in which a plurality of the biocompatible polymer blocks are arranged in gaps between a plurality of cells.

2. Description of the Related Art

Currently, there has been researched a trophic factor therapy in which a cell is locally administered such that a treatment is performed by a trophic factor produced by the cell. As the trophic factor therapy, in a case where cells are locally administered, it is attempted to administer the cells to be locally administered as a cell mass in order to cause the cells to remain and be engrafted in an administered portion.

In JONI H. YLOSTALO, et al., STEM CELLS 2012; 30:2283-2296, it is disclosed that human mesenchymal stem/interstitial cells cultured as spheroids are self-activated so as to produce prostaglandin E2. In Thomas J. Bartosh et al., PNAS, Aug. 3, 2010, vol. 107, no. 31, 13724-13729, it is disclosed that spheroids of human mesenchymal stromal cells secrete TSG-6 which is an anti-inflammatory protein.

In JP4819356B, fine particles mainly including biocompatible and biodegradable materials are disclosed. The biocompatible and biodegradable materials have transplantation cell on a surface, and the fine particle includes at least one active material that is implanted into the fine particle and that is active with respect to a cell in a case of the implantation or environment thereof. The fine particle has a diameter of 10 to 500 μm and further includes coating of a cell adhesive compound. The active material is selected from the group consisting of growth factors, hormones, and cytokines and is sustained by fine particles and controlled to be released.

Recently, research on regenerative medicine and cell treatment using mesenchymal stem cells (MSC) has been actively conducted. Among them, the therapeutic effect on intractable inflammatory diseases has attracted attention as a target, and various kinds of research have been conducted. For example, in JP2009-007321A, a method for preventing/treating inflammatory bowel disease by intravenously administering MSC is disclosed. Several clinical research and clinical trials also have been conducted. However, it has been found that a practically sufficient therapeutic effect cannot be exhibited (Aliment Pharmacol Ther 2017; 45: 205-221). Research also has been conducted to increase the anti-inflammatory ability by gene introduction into MSC (Inflamm. Res. (2015) 64:671-681). However, introducing genes into the cells is not necessarily a desirable option considering the effect thereof on the effectiveness and safety.

In WO2011/108517A, a cell structure that includes a polymer block having biocompatibility and a cell and in which the plurality of polymer blocks are disposed in gaps between the plurality of cells is disclosed. In the cell structure disclosed in WO2011/108517A, nutrient delivery from the outside to the inside of the cell structure is possible. In JP2015-134193A, a cell structure for cell transplantation that includes a polymer block having biocompatibility and at least one type of cells and in which the plurality of polymer blocks are disposed in gaps between the plurality of cells is disclosed. In the example of JP2015-134193A, it is disclosed that angiogenesis can be performed with the cell structure for cell transplantation.

SUMMARY OF THE INVENTION

As the cell transplantation treatment, several treatments have been known by promoting the regeneration of the host by a trophic factor (such as cytokine) released by the transplanted cells. For example, mesenchymal stem cells have been known to release cytokines having anti-inflammatory effects. However, cytokines are not sufficiently released by cell-only transplantation, and the desired effect cannot be obtained in many cases. An object of the present invention is to provide a trophic factor releasing agent having an increased amount of a trophic factor released by cells, compared with the case of using a cell mass. In addition, another object of the present invention is to provide an inflammatory disease treating agent.

As a result of intensive research to solve the above problems, the present inventors have found that, with respect to the cell structure that includes a biocompatible polymer block and a cell and in which a plurality of biocompatible polymer blocks are arranged in the gaps between the plurality of cells, the amount of the trophic factor released by the cell is increased compared with the case of the cell mass not including the biocompatible polymer block, and the cell structure is useful for treating inflammatory diseases, so as to complete the present invention.

That is, according to the present invention, the following inventions are provided.

<1> A trophic factor releasing agent comprising: a cell structure that includes biocompatible polymer blocks and cells and in which a plurality of the biocompatible polymer blocks are disposed in gaps between a plurality of the cells, in which a size of one of the biocompatible polymer blocks is 20 μm to 200 μm, and trophic factors are released from the cells.

<2> The trophic factor releasing agent according to <1>, in which a size of one of the biocompatible polymer blocks is 50 μm to 120 μm.

<3> The trophic factor releasing agent according to <1> or <2>, in which, in the biocompatible polymer block, a biocompatible polymer is cross-linked by heat, ultraviolet rays, or an enzyme.

<4> The trophic factor releasing agent according to any one of <1> to <3>, in which the biocompatible polymer block has an amorphous shape.

<5> The trophic factor releasing agent according to any one of <1> to <4>, in which the cell structure includes 0.0000001 µg to 1 µg of biocompatible polymer blocks per cell.

<6> The trophic factor releasing agent according to any one of <1> to <5>, in which the cell is a somatic stem cell.

<7> The trophic factor releasing agent according to any one of <1> to <6>, in which the trophic factor is cytokine.

<8> The trophic factor releasing agent according to any one of <1> to <7>, in which a biocompatible polymer is gelatin, collagen, atelocollagen, elastin, fibronectin, pronectin, laminin, tenascin, fibrin, fibroin, entactin, thrombospondin, RETRONECTIN (registered trademark), polylactic acid, polyglycolic acid, a lactic acid/glycolic acid copolymer, hyaluronic acid, glycosaminoglycan, proteoglycan, chondroitin, cellulose, agarose, carboxymethyl cellulose, chitin, or chitosan.

<9> The trophic factor releasing agent according to any one of <1> to <8>, in which a biocompatible polymer is recombinant gelatin.

<10> The trophic factor releasing agent according to <9>, in which the recombinant gelatin is represented by Formula 1, A-[(Gly-X-Y)$_n$]$_m$-B    Formula 1: 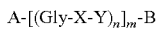

in the formula, A represents any amino acid or amino acid sequence, B represents any amino acid or amino acid sequence, n X's each independently represent any amino acid, n Y's each independently represent any amino acid, n represents an integer of 3 to 100, m represents an integer of 2 to 10, and n pieces of Gly-X-Y may be the same as or different from each other.

<11> The trophic factor releasing agent according to <9> or <10>, in which the recombinant gelatin is:
(1) a peptide formed of an amino acid sequence described in SEQ ID No: 1;
(2) a peptide which is formed of an amino acid sequence in which one or several amino acids are deleted, substituted, or added in the amino acid sequence described in SEQ ID No: 1, and has biocompatibility; or
(3) a peptide which is formed of an amino acid sequence having 80% or more sequence identity with the amino acid sequence described in SEQ ID NO: 1 and has biocompatibility.

<12> An inflammatory disease treating agent comprising: the trophic factor releasing agent according to any one of <1> to <11>.

<13> An inflammatory disease treating agent comprising: a cell structure that includes biocompatible polymer blocks and mesenchymal stem cells and in which a plurality of the biocompatible polymer blocks are disposed in gaps between a plurality of the mesenchymal stem cell, in which a size of one of the biocompatible polymer blocks is 20 µm to 200 µm.

<14> The inflammatory disease treating agent according to <13>, in which a size of one of the biocompatible polymer blocks is 50 µm to 120 µm.

<15> The inflammatory disease treating agent according to <13> or <14>, in which, in the biocompatible polymer block, a biocompatible polymer is cross-linked by heat, ultraviolet rays, or an enzyme.

<16> The inflammatory disease treating agent according to any one of <13> to <15>, in which the biocompatible polymer block has an amorphous shape.

<17> The inflammatory disease treating agent according to any one of <13> to <16>, in which the cell structure includes 0.0000001 µg to 1 µg of biocompatible polymer blocks per cell.

<18> The inflammatory disease treating agent according to any one of <13> to <17>, in which the mesenchymal stem cell is an adipose derived mesenchymal stem cell or a bone marrow derived mesenchymal stem cell.

<19> The inflammatory disease treating agent according to any one of <13> to <18>, in which a biocompatible polymer is gelatin, collagen, atelocollagen, elastin, fibronectin, pronectin, laminin, tenascin, fibrin, fibroin, entactin, thrombospondin, RETRONECTIN (registered trademark), polylactic acid, polyglycolic acid, a lactic acid/glycolic acid copolymer, hyaluronic acid, glycosaminoglycan, proteoglycan, chondroitin, cellulose, agarose, carboxymethyl cellulose, chitin, or chitosan.

<20> The inflammatory disease treating agent according to any one of <13> to <19>, in which a biocompatible polymer is recombinant gelatin.

<21> The inflammatory disease treating agent according to <20>, in which the recombinant gelatin is represented by Formula 1, A-[(Gly-X-Y)$_n$]$_m$-B    Formula 1: 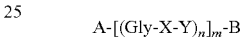

in the formula, A represents any amino acid or amino acid sequence, B represents any amino acid or amino acid sequence, n X's each independently represent any amino acid, n Y's each independently represent any amino acid, n represents an integer of 3 to 100, m represents an integer of 2 to 10, and n pieces of Gly-X-Y may be the same as or different from each other.

<22> The inflammatory disease treating agent according to <20> or <21>, in which the recombinant gelatin is:
(1) a peptide formed of an amino acid sequence described in SEQ ID No: 1;
(2) a peptide which is formed of an amino acid sequence in which one or several amino acids are deleted, substituted, or added in the amino acid sequence described in SEQ ID No: 1, and has biocompatibility; or
(3) a peptide which is formed of an amino acid sequence having 80% or more sequence identity with the amino acid sequence described in SEQ ID NO: 1 and has biocompatibility.

<23> The inflammatory disease treating agent according to any one of <13> to <22>, in which the mesenchymal stem cell is a human or dog derived mesenchymal stem cell.

According to the present invention, the following inventions are further provided.

(A) A method of releasing trophic factors, comprising: a step of transplanting a cell structure that includes biocompatible polymer blocks and cells and in which the plurality of biocompatible polymer blocks are disposed in gaps between the plurality of cells, and a size of one of the biocompatible polymer blocks is 20 µm to 200 µm to a subject in need of the trophic factors.

(B) A method of treating inflammatory disease, comprising: a step of transplanting a cell structure that includes biocompatible polymer blocks and cells and in which the plurality of biocompatible polymer blocks are disposed in gaps between the plurality of cells, and a size of one of the biocompatible polymer blocks is 20 µm to 200 µm.

(C) A cell structure for trophic factor release and/or trophic factor release, which includes biocompatible polymer blocks and cells and in which the plurality of biocompatible polymer blocks are disposed in gaps between the plurality of cells, and a size of one of the biocompatible polymer blocks is 20 μm to 200 μm.

(D) A cell structure for an inflammatory disease treatment, which includes biocompatible polymer blocks and cells and in which the plurality of biocompatible polymer blocks are disposed in gaps between the plurality of cells, and a size of one of the biocompatible polymer blocks is 20 μm to 200 μm.

(E) A use of a cell structure for manufacturing a trophic factor releasing agent, which includes biocompatible polymer blocks and cells and in which the plurality of biocompatible polymer blocks are disposed in gaps between the plurality of cells, and a size of one of the biocompatible polymer blocks is 20 μm to 200 μm.

(F) A use of a cell structure for manufacturing an inflammatory disease treating agent, which includes biocompatible polymer blocks and cells and in which the plurality of biocompatible polymer blocks are disposed in gaps between the plurality of cells, and a size of one of the biocompatible polymer blocks is 20 μm to 200 μm.

According to the trophic factor releasing agent of the embodiment of the present invention and the inflammatory disease treating agent including the trophic factor releasing agent, compared with a case of using a cell mass, it is possible to increase an amount of trophic factors released by the cells. According to the inflammatory disease treating agent of the embodiment of the present invention, compared with a case of using a cell mass, it is possible to increase the effect of treating an inflammatory disease.

BRIEF DESCRIPTION OF THE DRAWINGS

FIG. 1 illustrates liquid temperature profiling of an experiment described in Condition A.

FIG. 2 illustrates liquid temperature profiling of an experiment described in Condition B.

DESCRIPTION OF THE PREFERRED EMBODIMENTS

Hereinafter, aspects for implementing the present invention are specifically described.

In the present specification, the cell structure used in the present invention may be referred to as a mosaic cell mass (cell mass in a mosaic shape). The expression "to" in the present specification refers to a range including numerical values before and after the expression as a minimum value and a maximum value.

The present invention relates to a trophic factor releasing agent including a cell structure that includes biocompatible polymer block and cells and in which the plurality of biocompatible polymer blocks are disposed in gaps between the plurality of cells, a size of one of the biocompatible polymer blocks is 20 μm to 200 μm, and trophic factors are released from the cells.

As provided in the following examples, as a result of the measurement of amounts of various released trophic factors by using a mosaic cell mass and a cell mass, an amount of the trophic factor released from the mosaic cell mass was greater than the release amount from the cell mass (Example 8). The present invention is not limited to any theories, but it is assumed that, since the degrees of increase of the release amount were different depending on the types of the trophic factors, as the cause of increasing the release amount of the trophic factors, the effect of increasing a release amount was exhibited not only by the increase in the number of viable cells due to the mosaic cell mass but also by other causes.

As described in the following examples, an amount of the released TSG-6 was measured with the mosaic cell mass and the cell mass, and an amount of the trophic factors released from the mosaic cell mass was greater than the release amount from the cell mass (Example 11). In addition, the amount of the released TSG-6 was measured with the mosaic cell mass and the cell mass after TNFα stimulation, an amount of the trophic factors released from the mosaic cell mass was much greater than the release amount from the cell mass (Example 12).

In JONI H. YLOSTALO, et al., STEM CELLS 2012; 30:2283-2296 and Thomas J. Bartosh et al., PNAS, Aug. 3, 2010, vol. 107, no. 31, 13724-13729, it is disclosed that spheroids (cell masses) of human mesenchymal stem/interstitial cells produce trophic factors, but there is no disclosure of the mosaic cell mass. In JP4819356B, it is disclosed that the fine particles including biocompatible and biodegradable materials as main components include active materials selected from the group consisting of hormones and cytokines, but the active material is not released from the cell. However, in JP4819356B, there is no disclosure that the cells produce trophic factors. In JP2009-007321A, a mosaic cell mass is disclosed, but there is no disclosure that trophic factors are released from cells.

Figure 6:
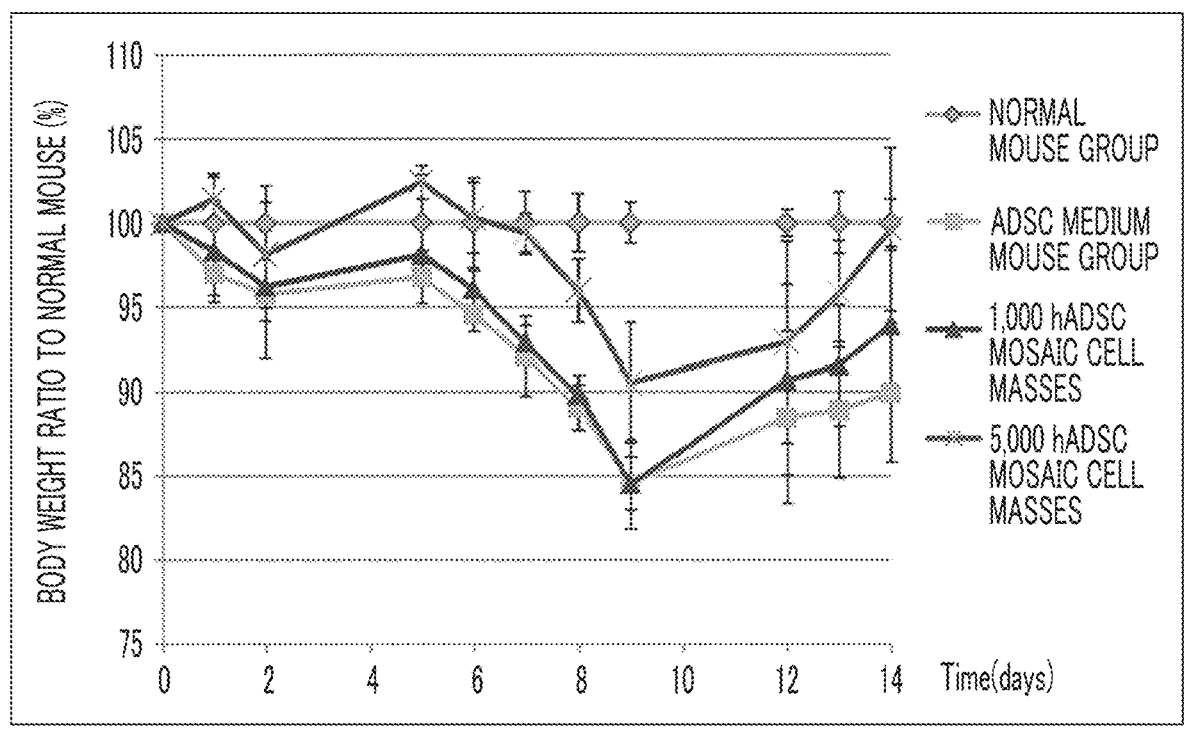
FIG. 6 illustrates results obtained by measuring body weights of a 2.5 mass % dextran sodium sulfate (DSS)-induced mice.

In FIG. 6 of JONI H. YLOSTALO, et al, STEM CELLS 2012; 30: 2283-2296 and FIG. 6 of Thomas J. Bartosh et al., PNAS, Aug. 3, 2010, vol. 107, no. 31, 13724-13729, it is illustrated that a production amount of the trophic factor of the spheroid is greater than that of the planar culture.

Generally, it is considered that the nutritional state of the cell in the planar culture is more satisfactory than that in the spheroid, and thus it is assumed that the production amount of trophic factors does not depend on the nutritional status of the cells. In JP2009-007321A, it is disclosed that the nutritional state of the mosaic cell mass is more satisfactory than that of the spheroid, but it is assumed that the trophic factor production amount does not depend on the nutritional state of the cells. Therefore, the effect of the present invention cannot be expected from the disclosure of JONI H. YLOSTALO, et al, STEM CELLS 2012; 30: 2283-2296 and JP4819356B.

As described above, with respect to the cell structure that includes the biocompatible polymer blocks and the cells and in which the plurality of biocompatible polymer blocks are disposed in the gaps between the plurality of cells, that effect that the release amount of the trophic factors from the cells is greater than the case of the cell mass cannot be expected from the related art.

(1) Biocompatible Polymer Block (1-1) Biocompatible Polymer

Biocompatibility means that, in a case of being brought into contact with a living body, it does not give a rise to a remarkable adverse reaction such as long-term and chronic inflammatory reaction. Whether or not the biocompatible polymers used in the present invention are decomposed within a living body is not particularly limited as long as the biocompatible polymers have affinity to the living body. However, biodegradable macromolecules are preferable. Specific examples of non-biodegradable materials include polytetrafluoroethylene (PTFE), polyurethane, polypropylene, polyester, vinyl chloride, polycarbonate, acryl, stainless steel, titanium, silicone, and 2-methacryloyloxyethyl phosphorylcholine (MPC). Specific examples of the biodegradable material include a polypeptide (for example, gelatin described below) such as naturally occurring peptide, recombinant peptide, or chemically synthesized peptide, polylactic acid, polyglycolic acid, a lactic acid/glycolic acid copolymer (PLGA), hyaluronic acid, glycosaminoglycan, proteoglycan, chondroitin, cellulose, agarose, carboxymethyl cellulose, chitin, and chitosan. Among these, a recombinant peptide is particularly preferable. Devising of an improvement of cell adhesion properties in these biocompatible polymers may be performed. Specifically, methods of "coating with the cell adhering substrate (fibronectin, vitronectin, laminin) and the cell adhesion sequence (RGD sequence, LDV sequence, REDV sequence, YIGSR sequence, PDSGR sequence, RYVVLPR sequence, LGTIPG sequence, RNIAEIIKDI sequence, IKVAV sequence, LRE sequence, DGEA sequence, and HAV sequence expressed by an amino acid single letter) peptide", "amination and cationization of the substrate surface", or "plasma treatment of the substrate surface" can be used.

The type of the recombinant peptide or the polypeptide including the chemically synthesized peptide is not particularly limited as long as the peptide has biocompatibility. For example, gelatin, collagen, atelocollagen, elastin, fibronectin, pronectin, laminin, tenascin, fibrin, fibroin, entactin, thrombospondin, and RETRONECTIN (registered trademark) are preferable, and gelatin, collagen, and atelocollagen are most preferable. Gelatin for use in the present invention is preferably natural gelatin, recombinant gelatin, or chemically synthesized gelatin and more preferably recombinant gelatin. The natural gelatin referred to herein means gelatin produced using naturally derived collagen.

Chemically synthesized peptide or chemically synthesized gelatin means artificially synthesized peptide or gelatin. The synthesis of a peptide such as gelatin may be solid phase synthesis or liquid phase synthesis, but is preferably solid phase synthesis. The solid phase synthesis of a peptide is well-known to those skilled in the art, and examples thereof include a fluorenyl-methoxy-carbonyl group (Fmoc group) synthesis method in which a Fmoc group is used for protection of an amino group, and a tert-butyl oxy carbonyl group (Boc group) synthesis method in which a Boc group is used for protection of an amino group. In the preferred embodiment of the chemically synthesized gelatin, the contents described in the recombinant gelatin described below in the present specification can be applied.

A "1/IOB" value which is a hydrophilicity value of the biocompatible polymer used in the present invention is preferably 0 to 1.0, more preferably within a range of 0 to 0.6, and still more preferably within a range of 0 to 0.4. IOB is an index of hydrophilic and hydrophobic properties based on an organic conceptual diagram representing polarity and non-polarity of an organic compound proposed by Atsushi HUJITA, and the details thereof are described in, for example, "Pharmaceutical Bulletin", vol. 2, 2, pp. 163 to 173 (1954), "Area of Chemistry" vol. 11, 10, pp. 719 to 725 (1957), and "Fragrance Journal, vol. 50, pp. 79 to 82 (1981). Briefly, the root of every organic compound is set to methane ($CH_4$), and all of other organic compounds are regarded as derivatives of methane. Certain numerical values for the number of carbons thereof, a substituent group, a transformation portion, a ring, and the like are set, and an organic value (OV) and an inorganic value (IV) are obtained by adding the score thereof. These values are plotted on a diagram in which the organic value is represented on the X-axis and the inorganic value is represented on the Y-axis. LOB in the organic conceptual diagram refers to a ratio of the inorganic value (IV) to the organic value (OV) in the organic conceptual diagram, that is, "inorganic value (IV)/organic value (OV)". The details of the organic conceptual diagram can be referred to "New Edition Organic Conceptual Diagram—Foundation and Application—" (written by Yoshio KOUDA, Sankyo Shuppan Co., Ltd., 2008). In the present specification, the hydrophilic and hydrophobic properties are represented by a "MOB" value which was obtained by taking a reciprocal number of JOB. This is a notation of representing more hydrophilic properties as the "1/IOB" value becomes small (close to 0).

In a case where the "1/IOB" value of the polymer used in the present invention is caused to be in the range described above, the hydrophilic properties and water absorbency become high, and thus it is assumed that the "1/IOB" value effectively acts to hold nutrient components and contributes to the stability and survival of cells in the cell structure (mosaic cell mass) according to the present invention.

In a case where the biocompatible polymers used in the present invention are polypeptides, the hydrophilic and hydrophobic indexes represented by a grand average of hydropathicity (GRAVY) value are preferably −9.0 to 0.3, and more preferably −7.0 to 0.0. The grand average of hydropathicity (GRAVY) value can be obtained by methods of "Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Human Press (2005). pp. 571 to 607" and "Gasteiger E., Gattiker A., Hoogland C., Ivanyi I., Appeal R. D., Bairoch A.; ExPASy: the proteomics server for in-depth protein knowledge and analysis.; Nucleic Acids Res. 31:3784-3788 (2003)".

In a case where the GRAVY value of the polymer used in the present invention is caused to be in the range described above, the hydrophilic properties and water absorbency become high, and thus it is assumed that the GRAVY value effectively acts to hold nutrient components and contributes to the stability and survival of cells in the cell structure (mosaic cell mass) according to the present invention.

(1-2) Cross-Linking

The biocompatible polymers used in the present invention may be or may not be cross-linked, but are preferably cross-linked. By using the cross-linked biocompatible polymers, it is possible to obtain an effect of preventing instant decomposition during culturing in a medium and during transplantation into a living body. As general cross-linking methods, thermal cross-linking, cross-linking using aldehydes (for example, formaldehyde or glutaraldehyde), cross-linking using a condensation agent (carbodiimide, cyanamide, or the like), enzymatic cross-linking, photocrosslinking, ultraviolet cross-linking, a hydrophobic interaction, hydrogen bonding, an ionic interaction, and the like are known, it is also possible to use the above-described cross-linking methods of the present invention. As the cross-linking methods used in the present invention, thermal cross-linking, ultraviolet cross-linking, or enzymatic cross-linking is more preferable, and thermal cross-linking is particularly preferable.

In a case of performing cross-linking using an enzyme, there is no particular limitation as long as the enzyme has a cross-linking action between polymer materials. However, it is possible to perform cross-linking preferably using transglutaminase and laccase and most preferably using transglutaminase. Specific examples of protein to be subjected to enzymatic cross-linking using transglutaminase are not particularly limited as long as the protein has a lysine residue and a glutamine residue. Transglutaminase may be derived from a mammal or may be derived from a microorganism. Specific examples thereof include mammal derived transglutaminase which has been sold as Activa series manufactured by Ajinomoto Co., Inc., and a reagent; guinea pig liver derived transglutaminase manufactured by, for example, Oriental Yeast Co., Ltd., Upstate USA Inc., or Biodesign International, Inc.; goat derived transglutaminase; rabbit derived transglutaminase; and human derived blood coagulation factors (Factor XIIIa: Haematologic Technologies, Inc).

The reaction temperature in a case of performing cross-linking (for example, thermal cross-linking) is not particularly limited as long as cross-linking can be performed, but is preferably −100° C. to 500° C., more preferably 0° C. to 300° C., still more preferably 50° C. to 300° C., particularly preferably 100° C. to 250° C., and most preferably 120° C. to 200° C.

(1-3) Recombinant Gelatin

The recombinant gelatin referred in the present invention means polypeptides or protein-like substances which have an amino acid sequence similar to that of gelatin produced through gene recombination technology. The recombinant gelatin which can be used in the present invention preferably has a repetition of a sequence (X and Y each independently show any amino acids) represented by Gly-X-Y which is characteristic to collagen. Here, a plurality of pieces of Gly-X-Y may be the same as or different from each other. Preferably, two or more sequences of cell adhesion signals are included in one molecule. As the recombinant gelatin used in the present invention, it is possible to use recombinant gelatin having an amino acid sequence derived from a partial amino acid sequence of collagen, it is possible to use recombinant gelatin disclosed in, for example, EP1014176, U.S. Pat. No. 6,992,172B, WO2004/085473A, and WO2008/103041A, but the recombinant gelatin is not limited thereto. Preferred recombinant gelatin used in the present invention is recombinant gelatin of the following aspect.

The recombinant gelatin is excellent in biocompatibility with original performance of natural gelatin, and is excellent in non-infection properties since there is no concern of bovine spongiform encephalopathy (BSE) and the recombinant gelatin with not being naturally derived. The recombinant gelatin is even compared to natural gelatin, and a sequence is determined. Therefore, it is possible to accurately design the strength and degradability so as to reduce deviation through cross-linking or the like.

The molecular weight of recombinant gelatin is not particularly limited, but is preferably 2,000 to 100,000 (2 kDa (kilodaltons) to 100 kDa), more preferably 2,500 to 95,000 (2.5 kDa to 95 kDa), still more preferably 5,000 to 90,000 (5 kDa to 90 kDa), and most preferably 10,000 to 90,000 (10 kDa to 90 kDa).

The recombinant gelatin preferably has a repetition of a sequence represented by Gly-X-Y which is characteristic of collagen. Here, a plurality of pieces of Gly-X-Y may be the same as or different from each other. In Gly-X-Y, Gly represents glycine and X and Y represent any amino acid (preferably represents any amino acid other than glycine). The sequence represented by Gly-X-Y characteristic to collagen is a partial structure which is extremely specific compared to other protein in a composition or a sequence of an amino acid of gelatin/collagen. In this section, glycine occupies about one third of the entirety of the amino acid sequence, one sequence is repeated every three sequences. Glycine is the simplest amino acid. Therefore, there is a little restraint in arrangement of molecular chains and glycine significantly contributes to regeneration of a helix structure during gelation. It is preferable that amino acids represented by X and Y contain many imino acids (proline and oxyproline) and occupy 10% to 45% of the entirety of the sequence. Preferably 80% or more of the sequence of the amino acids, more preferably 95% or more of the sequence of the amino acids, and most preferably 99% or more of the sequence of the amino acids in the recombinant gelatin have a repeating structure of Gly-X-Y.

In general gelatin, a polar amino acid with an electrical charge and a polar non-charged amino acid exist by 1:1 in polar amino acids. Here, the polar amino acid specifically indicates cysteine, aspartic acid, glutamic acid, histidine, lysine, asparagine, glutamine, serine, threonine, tyrosine, or arginine. Among these, the polar non-charged amino acid indicates cysteine, asparagine, glutamine, serine, threonine, or tyrosine. In recombinant gelatin used in the present invention, the proportion of the polar amino acid in the whole constituent amino acid is 10% to 40% and preferably 20% to 30%. It is preferable that the proportion of a non-charged amino acid in the polar amino acid is greater than or equal to 5% and less than 20% and preferably greater than or equal to 5% and less than 10%. It is preferable that any one amino acid or preferably two or more amino acids among serine, threonine, asparagine, tyrosine, and cysteine are not contained on a sequence.

In general, in polypeptides, minimum amino acid sequences which work as cell adhesion signals are known (for example, Nagai Shoten Co., Ltd., "Pathophysiology", Vol. 9, No. 7 (1990) p. 527). The recombinant gelatin used in the present invention preferably has two or more these cell adhesion signals in one molecule. As the specific sequences, sequences such as an RGD sequence, an LDV sequence, an REDV sequence (SEQ ID NO:2), a YIGSR sequence (SEQ ID NO:3), a PDSGR sequence (SEQ ID NO:4), an RYVVLPR sequence (SEQ ID NO:5), an LGTIPG sequence (SEQ ID NO:6), an RNIAEIIKDI sequence (SEQ ID NO:7), an IKVAV sequence (SEQ ID NO:8), an LRE sequence, a DGEA sequence (SEQ ID NO:9), and a HAV sequence, which are represented by one-letter notation of amino acids are preferable in that there are many kinds of cells adhered. An RGD sequence, a YIGSR sequence (SEQ ID NO:3), a PDSGR sequence (SEQ ID NO:4), an LGTIPG sequence (SEQ ID NO:6), an IKVAV sequence (SEQ ID NO:8), and a HAV sequence are more preferable and an RGD sequence is particularly preferable. In the RGD sequence, an ERGD sequence (SEQ ID NO:10) is preferable. It is possible to improve the production amount of substrate of a cell using recombinant gelatin having cell adhesion signals.

As the disposition of RGD sequences in recombinant gelatin used in the present invention, it is preferable that the number of amino acids between RGDs is not uniform between 0 and 100, and it is more preferable that the number of amino acids between RGDs is not uniform between 25 and 60.

The content of this minimum amino acid sequence is preferably 3 to 50, more preferably 4 to 30, particularly preferably 5 to 20, and most preferably 12 in one molecule of protein in view of cell adhesion properties and proliferation properties.

In recombinant gelatin used in the present invention, the proportion of RGD motifs with respect to the total number of amino acids is preferably at least 0.4%. In a case where recombinant gelatin contains 350 or more amino acids, each stretch of the 350 amino acids preferably contains at least one RGD motif. The proportion of RGD motifs is more preferably at least 0.6%, even more preferably at least 0.8%, still even more preferably at least 1.0%, particularly preferably at least 1.2%, and most preferably at least 1.5% with respect to the total number of amino acids. The number of RGD motifs within a recombinant peptide is preferably at least 4, more preferably 6, even more preferably 8, and particularly preferably 12 to 16 per 250 amino acids. The proportion of RGD motifs being 0.4% corresponds to at least one RGD sequence per 250 amino acids. The number of RGD motifs is an integer, and therefore, gelatin formed of 251 amino acids needs to contain at least two RGD sequences in order to satisfy the characteristics of 0.4%. It is preferable that the recombinant gelatin of the present invention contains at least two RGD sequences per 250 amino acids, more preferably contains at least three RGD sequences per 250 amino acids, and still more preferably contains at least four RGD sequences per 250 amino acids. As another aspect of the recombinant gelatin of the present invention, the recombinant gelatin preferably includes at least 4 RGD motifs, preferably includes 6 RGD motifs, even more preferably includes 8 RGD motifs, and particularly preferably includes 12 to 16 RGD motifs.

In addition, the recombinant gelatin may be partially hydrolyzed.

The recombinant gelatin used in the present invention is preferably represented by Formula 1: A-[(Gly-X-Y)$_n$]$_m$-B. n pieces of X each independently represent any amino acid and n pieces of Y each independently represent any amino acid. m preferably represents an integer of 2 to 10 and more preferably represents an integer of 3 to 5. n is preferably an integer of 3 to 100, more preferably an integer of 15 to 70, and most preferably an integer of 50 to 65. A represents any amino acid or an amino acid sequence, B represents any amino acid or an amino acid sequence. n pieces of Gly-X-Y may be the same as or different from each other.

More preferably, the recombinant gelatin used in the present invention is represented by Gly-Ala-Pro-[(Gly-X-Y)$_{63}$]$_3$-Gly (SEQ ID NO:11) (in the formula, 63 pieces of X each independently represent any amino acid and 63 pieces of Y each independently represent any amino acid. 63 pieces of Gly-X-Y may be the same as or different from each other).

It is preferable that a plurality of sequence units of collagen which naturally exists are bonded to a repeating unit. Any naturally existing collagen referred to herein may be used as long as the collagen naturally exists, but is preferably I type collagen, II type collagen, III type collagen, IV type collagen, or V type collagen, and more preferably I type collagen, II type collagen, or III type collagen. According to another form, the above-described collagen is preferably derived from a human-type, cattle, a pig, a mouse, or a rat, and is more preferably derived from a human-type.

An isoelectric point of the recombinant gelatin used in the present invention is preferably 5 to 10, more preferably 6 to 10, and still more preferably 7 to 9.5. The measurement of the isoelectric point of the recombinant gelatin can be carried out by measuring the pH after passing a 1 mass % gelatin solution through a mixed crystal column of a cation-anion exchange resin above-described disclosed in isoelectric focusing method (refer to Maxey, C. R. (1976; Phitogr. Gelatin 2, Editor Cox, P. J. Academic, London, Engl.)).

It is preferable that the recombinant gelatin is not deaminated.

It is preferable that the recombinant gelatin does not have a telopeptide.

It is preferable that the recombinant gelatin is a substantially pure polypeptide which is prepared using a nucleic acid encoding an amino acid sequence.

It is particularly preferable that the recombinant gelatin used in the present invention is any of (1) a peptide formed of an amino acid sequence described in SEQ ID No: 1;

(2) a peptide which is formed of an amino acid sequence in which one or several amino acids are deleted, substituted, or added in the amino acid sequence described in SEQ ID No: 1, and has biocompatibility; or (3) a peptide which is formed of an amino acid sequence having 80% or more (more preferably 90% or more, particularly preferably 95% or more, and most preferably 98% or more) sequence identity to the amino acid sequence described in SEQ ID No: 1, and has biocompatibility.

The sequence identity of the present invention refers to a value calculated in the following equation.

% Sequence identity=[(the number of identical residues)/(alignment length)]×100

The sequence identity between two amino acid sequences can be determined by any method well-known to those skilled in the art and can be determined by the Basic Local Alignment Search Tool (BLAST) program (J. Mol. Biol. 215: 403 to 410, 1990) or the like.

"One or several" in the expression "amino acid sequence in which one or several amino acids are deleted, substituted, or added" preferably means 1 to 20 amino acids, more preferably means 1 to 10 amino acids, still more preferably means 1 to 5 amino acids, and particularly preferably means 1 to 3 amino acids.

The recombinant gelatin used in the present invention can be produced through gene recombination technology which is known to those skilled in the art, and can be produced in accordance with, for example, methods disclosed in EP1014176A2, U.S. Pat. No. 6,992,172B, WO2004/085473A, and WO2008/103041A. Specifically, a gene encoding an amino acid sequence of predetermined recombinant gelatin is acquired, the acquired gene is incorporated into an expression vector to manufacture a recombinant expression vector, and a transformant is manufactured by introducing the recombinant expression vector into an appropriate host. The recombinant gelatin is produced by culturing the obtained transformant in an appropriate medium. Therefore, it is possible to prepare the recombinant gelatin used in the present invention by collecting the recombinant gelatin produced from a culture product.

(1-4) Biocompatible Polymer Block

In the present invention, a block (aggregation) formed of the above-described biocompatible polymers is used.

The shape of the biocompatible polymer block of the present invention is not particularly limited. Examples thereof include an amorphous shape, a spherical shape, a particulate shape (granule), a powdery shape, a porous shape, a fibrous shape, a spindle shape, a flat shape, and a sheet shape. An amorphous shape, a spherical shape, a particulate shape (granule), a powdery shape, and a porous shape are preferable. The amorphous shape indicates that the shape of a surface is uneven, and indicates, for example, an object, such as rock, which has roughness. Examples of the above-described shapes are not distinct from each other. For example, in some cases, an example of a subordinate concept of the particulate shape (granule) is an amorphous shape.

The shape of the biocompatible polymer block of the present invention is not particularly limited as described above. However, the tap density is preferably 10 mg/cm$^3$ to 500 mg/cm$^3$, more preferably 20 mg/cm$^3$ to 400 mg/cm$^3$, still more preferably 40 mg/cm$^3$ to 220 mg/cm$^3$, and particularly preferably 50 mg/cm$^3$ to 150 mg/cm$^3$.

The tap density is a value indicating how much volume of block can be densely filled. It can be seen that, as the value becomes smaller, the block cannot be densely filled, that is, the structure of the block is complicated. It is considered that the tap density of the biocompatible polymer block indicates the complexity of a surface structure of the biocompatible polymer block and the amount of void formed in a case where biocompatible polymer blocks are collected as an aggregate. As the tap density becomes smaller, the void between biocompatible polymer blocks becomes larger and a grafted region of a cell becomes larger. In addition, in a case where the tap density is not too small, the biocompatible polymer block can appropriately exist between cells and nutrients can be delivered into a cell structure in a case where the cell structure is produced, and therefore, it is considered that it is preferable that the tap density falls within the above-described range.

The tap density referred to in the present specification can be measured as follows. A container (with a cylindrical shape with a diameter of 6 mm and a length of 21.8 mm: a capacity of 0.616 cm$^3$) (hereinafter, described as a cap) is prepared for the measurement of the tap density. First, the mass of only a cap is measured. Thereafter, a funnel is attached to the cap, and blocks are poured from the funnel so as to be collected in the cap. After placing a sufficient amount of block, the cap portion is hit 200 times on a hard object such as a desk, the funnel is removed, and the blocks are leveled with a spatula. The mass is measured in a state where the cap is filled up with the blocks. The tap density can be obtained by calculating the mass of only the blocks from the difference between the mass of the cap filled up with the blocks and the mass of only the cap, and dividing the mass of only the blocks by the volume of the cap.

The cross-linking degree of the biocompatible polymer block of the present invention is not particularly limited, but is preferably greater than or equal to 2, more preferably 2 to 30, still more preferably 4 to 25, and particularly preferably 4 to 22.

The method for measuring the cross-linking degree (the number of cross-linking times per molecule) of a biocompatible polymer block is not particularly limited. However, in a case where the biocompatible polymer is CBE3, for example, the measurement can be performed by a TNBS (2,4,6-trinitrobenzene sulfonic acid) method described in examples below. Specifically, a sample obtained by mixing biocompatible polymer blocks, a NaHCO$_3$ aqueous solution, and a TNBS aqueous solution, allowing the mixture to react for 3 hours at 37° C., and then, stopping the reaction, and a blank obtained by mixing biocompatible polymer blocks, a NaHCO$_3$ aqueous solution, and a TNBS aqueous solution and stopping a reaction immediately after the mixing were prepared. The cross-linking degree (the number of cross-linking times per molecule) can be calculated from (Formula 2) and (Formula 3) by measuring each absorbance (345 nm) of the sample and the blank which have been diluted with pure water.

$$(As-Ab)/14{,}600 \times V/w \quad \text{(Formula 2)}$$

(Formula 2) represents the amount (molar equivalent) of lysine per 1 g of biocompatible polymer blocks.

(in the formula, As represents the sample absorbance, Ab represents the blank absorbance, V represents the amount (g) of reaction liquid, and w represents the mass (mg) of the biocompatible polymer blocks.)

$$1-(\text{sample (Formula 2)/uncross-linked polymers (Formula 2)}) \times 34 \quad \text{(Formula 3)}$$

(Formula 3) represents the number of cross-linking times per molecule.

The water absorption rate of the biocompatible polymer block of the present invention is not particularly limited, but is preferably greater than or equal to 300%, more preferably greater than or equal to 400%, still more preferably greater than or equal to 500%, particularly preferably greater than or equal to 600%, and most preferably greater than or equal to 700%. The upper limit of the water absorption rate is not particularly limited, but is generally less than or equal to 4,000% or less than or equal to 2,000%.

The method for measuring the water absorption rate of the biocompatible polymer block is not particularly limited. However, the water absorption rate of the biocompatible polymer block can be measured, for example, through the method in examples to be described below. Specifically, a 3 cm×3 cm nylon mesh bag is filled with about 15 mg of biocompatible polymer blocks at 25° C. and is swollen in ion exchange water for 2 hours. Then, the biocompatible polymer blocks are dried with air for 10 minutes, and the mass is measured at each stage to obtain the water absorption rate according to (Formula 4).

$$\text{Water absorption rate}=(w2-w1-w0)/w0 \quad \text{(Formula 4)}$$

(in the formula, w0 represents the mass of a material before water absorption, w1 represents the mass of an empty bag after water absorption, and w2 represents the mass of the entirety of the bag containing the material after water absorption.)

The size of one biocompatible polymer block of the present invention is 20 μm to 200 μm, preferably 20 μm to 150 μm, more preferably 50 μm to 120 μm, and even more preferably 53 μm to 106 μm.

It is possible to favorably deliver nutrients into a cell structure from the outside by setting the size of one biocompatible polymer block to be within the above-described range. The size of one biocompatible polymer block does not mean that an average value of the sizes of a plurality of biocompatible polymer blocks is within the above-described range, but means the size of each biocompatible polymer block which is obtained by sieving a plurality of biocompatible polymer blocks.

The size of one block can be defined by the size of a sieve used in a case of dividing the block. For example, blocks remaining on a sieve with 106 μm in a case where blocks which have been passed through a sieve with 180 μm for sifting are sifted using the sieve with 106 μm can be regarded as blocks having a size of 106 to 180 μm. Next, blocks remaining on a sieve with 53 μm in a case where blocks which have been passed through the sieve with 106 μm for sifting are sifted using the sieve with 53 μm can be regarded as blocks having a size of 53 to 106 μm. Next, blocks remaining on a sieve with 25 μm in a case where blocks which have been passed through the sieve with 53 μm for sifting are sifted using the sieve with 25 μm can be regarded as blocks having a size of 25 to 53 μm.

(1-5) Method for Producing Biocompatible Polymer Block

The method for producing a biocompatible polymer block is not particularly limited. For example, it is possible to obtain a biocompatible polymer block by pulverizing a solid matter (such as a porous body of a biocompatible polymer) containing a biocompatible polymer using a pulverizer (such as NEW POWERMILL). The solid matter (such as a porous body of a biocompatible polymer) containing a biocompatible polymer can be obtained, for example, by freeze-drying an aqueous solution containing the biocompatible polymer.

It is possible to produce an amorphous biocompatible polymer block of which the shape of the surface is uneven, by pulverizing a solid matter containing a biocompatible polymer as described above.

The method for manufacturing the porous body of the biocompatible polymer is not particularly limited, but the porous body can also be obtained by freeze-drying an aqueous solution including the biocompatible polymer. For example, by including a freezing step in which the temperature (the highest internal liquid temperature) of the solution at a portion having the highest liquid temperature in the solution is the "solvent melting point −3° C." or lower in the unfrozen state, the ice to be formed can be caused to have a spherical shape. According to this process, by causing the ice to be dried, a porous body having spherical isotropic vacancies (spherical pores) can be obtained. For example, by performing freezing without including a freezing step in which the temperature (the highest internal liquid temperature) of the solution at a portion having the highest liquid temperature in the solution is the "solvent melting point −3° C." or higher in the unfrozen state, the ice to be formed can be caused to have a pillar/flat plate shape. In a case where the ice is dried according to this process, a porous body having pores (pillars/flat plate pores) in pillar or flat shapes which are long uniaxially or biaxially can be obtained. In the case where the porous body of the biocompatible polymer is pulverized to manufacture a biocompatible polymer block, the vacancies of the porous body before pulverization influence the shape of the biocompatible polymer block to be obtained, and thus the shape of the biocompatible polymer block to be obtained can be adjusted by adjusting the condition of freeze-drying as described above.

An example of the method for producing a porous body of a biocompatible polymer includes a method including (a) a step of cooling a solution of biocompatible polymers under the conditions where the difference between the temperature of a portion having the highest liquid temperature within the solution and the temperature of a portion having the lowest liquid temperature within the solution is lower than or equal to 2.5° C. and the temperature of a portion having the highest liquid temperature within the solution is lower than or equal to a melting point, to an unfrozen state, (b) a step of freezing the solution of the biocompatible polymers obtained in the step (a), and (c) a step of freeze-drying the frozen biocompatible polymers obtained in the step (b).

However, the present invention is not limited to the above method.

In a case where the solution of the biocompatible polymers is cooled to an unfrozen state, the variation in the size of obtained porous pores is reduced by making the difference between the temperature of a portion having the highest liquid temperature and the temperature of a portion having the lowest liquid temperature within the solution be lower than or equal to 2.5° C. (preferably lower than or equal to 2.3° C. and more preferably lower than or equal to 2.1° C.), that is, by reducing the difference in temperature. The lower limit of the difference between the temperature of a portion having the highest liquid temperature and the temperature of a portion having the lowest liquid temperature within the solution is not particularly limited, but may be higher than or equal to 0° C. For example, the lower limit thereof may be higher than or equal to 0.1° C., higher than or equal to 0.5° C., higher than or equal to 0.8° C., or higher than or equal to 0.9° C. Accordingly, the cell structure using the biocompatible polymer block manufactured with the manufactured porous body achieves the effect of exhibiting a large number of cells.

The cooling in the step (a) is preferably carried out, for example, using a material (preferably TEFLON (registered trademark)) having a lower thermal conductivity than water. The portion having the highest liquid temperature within the solution can be supposed as the farthest portion from a cooling side, and the portion having the lowest liquid temperature within the solution can be supposed as a liquid temperature of the cooling surface.

In the step (a), the difference between the temperature of a portion having the highest liquid temperature within the solution and the temperature of a portion having the lowest liquid temperature within the solution immediately before generation of solidification heat is preferably lower than or equal to 2.5° C., more preferably lower than or equal to 2.3° C., and still more preferably lower than or equal to 2.1° C. Here, the "difference in temperature immediately before the generation of solidification heat" means a difference in temperature in a case where the difference in temperature becomes largest between 1 second and 10 seconds before the generation of solidification heat.

In the step (a), the temperature of a portion having the lowest liquid temperature within the solution is preferably lower than or equal to a melting point of a solvent −5° C., more preferably lower than or equal to a melting point of a solvent −5° C. and higher than or equal to a melting point of a solvent −20° C., and still more preferably lower than or equal to a melting point of a solvent −6° C. and higher than or equal to a melting point of a solvent −16° C. The solvent of a melting point of a solvent is a solvent of a solution of biocompatible polymers.

In the step (b), the solution of the biocompatible polymers obtained in the step (a) is frozen. The cooling temperature for the freezing in the step (b) is not particularly limited. Depending on cooling equipment, the cooling temperature is preferably a temperature which is 3° C. to 30° C. lower than the temperature of a portion having the lowest liquid temperature within the solution, more preferably a temperature which is 5° C. to 25° C. lower than the temperature of a portion having the lowest liquid temperature within the solution, and still more preferably a temperature which is 10° C. to 20° C. lower than the temperature of a portion having the lowest liquid temperature within the solution.

In the step (c), the frozen biocompatible polymers obtained in the step (b) are freeze-dried. The freeze-drying can be performed through a usual method. For example, the freeze-drying can be performed by carrying out vacuum drying at a temperature lower than a melting point of a solvent and further carrying out vacuum drying at room temperature (20° C.).

In the present invention, a biocompatible polymer block can be preferably produced by pulverizing the porous body obtained in the above-described step (c).

(2) Cell

The types of the cells used in the present invention are not particularly limited, cells that release trophic factors which are the purpose of the present invention can be appropriately used, and any kinds of cells can be used according to an actual treatment purpose. In addition, one type of cell may be used, or a plurality of types of cells may be used in combination. Cells to be used are preferably animal cells, more preferably vertebrate derived cells, and particularly preferably human derived cells. The types of vertebrate derived cells (particularly, human-type derived cells) may be any of universal cells, somatic stem cells, precursor cells, and mature cells and particularly preferably somatic stem cells.

It is possible to use, for example, embryonic stem (ES) cells, germ-stem (GS) cells, or artificial pluripotent stem (iPS) cells as the universal cells. It is possible to use, for example, mesenchymal stem cells (MSC), hematopoietic stem cells, amniotic cells, umbilical cord blood cells, bone marrow derived cells (for example, bone marrow derived MSCs), myocardial stem cells, adipose derived stem cells, or neural stem cells can be used as the somatic stem cell. It is possible to use, for example, skin, dermis, epidermis, muscle, cardiac muscles, nerves, bones, cartilage, endothelium, brain, epithelium, heart, kidney, liver, pancreas, spleen, oral cavity, cornea, bone marrow, umbilical cord blood, amnion, or cells derived from hair as the precursor cells and the mature cells. It is possible to use, for example, ES cells, iPS cells, MSCs, chondrocytes, osteoblasts, osteoprecursor cells, mesenchymal cells, myoblasts, cardiac muscle cells, cardiomyoblasts, nerve cells, hepatocytes, beta cells, fibroblasts, corneal endothelial cells, vascular endothelial cells, corneal epithelial cells, amniotic cells, umbilical cord blood cells, bone marrow derived cells, or hematopoietic stem cells as the human-type derived cells. The cells may be derived from any of autologous cells and heterologous cells. Among these, it is preferable to use mesenchymal stem cells as the cells. Adipose derived mesenchymal stem cells or bone marrow derived mesenchymal stem cells are preferable as the mesenchymal stem cell. As a source of mesenchymal stem cells, a human or a dog is preferable.

(3) Cell Structure

The cell structure of the present invention is a cell structure that includes the biocompatible polymer block according to the present invention and at least one kind of cells and in which the plurality of biocompatible polymer blocks are disposed in gaps between the plurality of cells. According to the present invention, the biocompatible polymer blocks and the cells are used to three dimensionally dispose the plurality of polymer blocks in the gaps between the plurality of cells, the biocompatible polymer blocks and the cells are three dimensionally disposed in a mosaic shape, a cell three-dimensional structure in which cells uniformly exist in the structure is formed, and thus as described above, and material permeability is exhibited.

In the cell structure of the present invention, the plurality of polymer blocks are arranged in gaps between the plurality of cells. Here, the "gaps between cells" is not necessarily a space closed by the constituent cells, and may be interposed by the cells. Gaps are not necessarily present between all of the cells, and there may be a place where cells are brought into contact with each other. The distance of gaps between cells through polymer blocks, that is, the gap distance in a case of selecting a certain cell, and a cell existing in a shortest distance from the certain cell is not particularly limited. However, the distance is preferably the size of a polymer block, and a favorable distance is also within the range of the favorable size of a polymer block.

The polymer blocks according to the present invention have a configuration of being interposed by the cells. However, there are not necessarily cells between all of the polymer blocks, and there may be a place where polymer blocks are brought into contact with each other. The distance between polymer blocks through cells, that is, the distance in a case of selecting a polymer block, and a polymer block existing in a shortest distance from the polymer block is not particularly limited. However, the distance is preferably the size of an aggregation of cells in a case where one or several cells to be used are gathered. For example, the size thereof is 10 µm to 1,000 µm, preferably 10 µm to 100 µm, and more preferably 10 µm to 50 µm.

In the present specification, the expression "uniformly existing cells" such as "cell three-dimensional structure in which cells uniformly exist in the structure" is used, but it does not mean complete uniformity.

The thickness or the diameter of the cell structure of the present invention can be caused to be a desired thickness, but the lower limit is preferably 215 µm or more, more preferably 400 µm or more, and most preferably 730 µm or more. The upper limit of the thickness or the diameter is not particularly limited, but the general range in use is preferably 3 cm or less, more preferably 2 cm or less, and even more preferably 1 cm or less. The range of the thickness or the diameter of the cell structure is preferably 400 µm to 3 cm, more preferably 500 µm to 2 cm, and even more preferably 720 µm to 1 cm.

In the cell structure of the present invention, regions consisting of polymer blocks and regions consisting of cells are preferably disposed in a mosaic shape. In the present specification, the expression "the thickness or the diameter of the cell structure" means the followings. In a case where one point A in the cell structure is selected, in a straight line passing through the point A, a length of the line segment dividing the cell structure such that the distance from an outer boundary of the cell structure is the shortest is set as a line segment A. In the cell structure, the point A at which the line segment A becomes the longest is selected, a length of the line segment A in this case refers to "a thickness or a diameter of a cell structure".

In the cell structure of the present invention, the ratio of a polymer block to a cell is not particularly limited. However, the mass of a polymer block per cell is preferably 0.0000001 µg to 1 µg, more preferably 0.000001 µg to 0.1 µg, even more preferably 0.00001 µg to 0.01 µg, and most preferably 0.00002 µg to 0.006 µg. According to the range, it is possible to cause the cells to be more evenly exist. By setting the lower limit to be within the range, it is possible to exhibit an effect of the cells in a case of using the cells for a desired purpose. Moreover, by setting the upper limit to be within the above-described range, it is possible to supply components in arbitrarily existing polymer blocks to cells. Here, the components in polymer blocks are not particularly limited, but examples thereof include components contained in a medium described below.

(4) Method for Producing Cell Structure

The cell structure used in the present invention can be manufactured by mixing a biocompatible polymer block and at least one type of cells. Specifically, the cell structure of the embodiment of the present invention can be manufactured by alternately disposing the biocompatible polymer blocks (masses consisting of biocompatible polymers) and the cells. The manufacturing method is not particularly limited, but is preferably a method of seeding cells after a polymer block is formed. Specifically, cell structures can be manufactured by incubating a mixture of the biocompatible polymer blocks and a cell-containing culture solution. For example, the cells and the biocompatible polymer blocks manufactured in advance are arranged in a mosaic shape in a container or in a solution held in a container. As means of disposition, it is preferable to promote and control mosaic-like disposition consisting of the cells and the biocompatible substrate by using natural aggregation, natural falling, centrifugation, and stirring.

The container to be used is preferably a container consisting of a cell low adhesive material or a cell non-adhesive material and more preferably a container consisting of polystyrene, polypropylene, polyethylene, glass, polycarbonate, and polyethylene terephthalate. The shape of the bottom surface of the container is preferably a flat bottom shape, a U shape, or a V shape.

With respect to the mosaic-like cell structure obtained by the method, for example, a cell structure having a desired size can be manufactured by a method such as (a) fusing separately adjusted mosaic-like cell masses or (b) voluming up under a differentiation medium or a proliferation medium. The fusing method and the voluming-up method are not particularly limited.

For example, in the step of incubating the mixture of the biocompatible polymer blocks and the cell-containing culture solution, the cell structure can be volume up by replacing the medium with a differentiation medium or a proliferation medium. Preferably, in the step of incubating the mixture of the biocompatible polymer blocks and the cell-containing culture solution, by further adding the biocompatible polymer block, it is possible to manufacture a cell structure which is a cell structure having a desired size and a cell structure in which cells uniformly exist in a cell structure.

Specifically, the method of fusing separately adjusted mosaic-like cell masses includes a method of manufacturing a cell structure including a step of fusing a plurality of cell structures that include a plurality of biocompatible polymer blocks and a plurality of cells and in which one or the plurality of biocompatible polymer blocks are arranged in a portion or all of gaps formed by the plurality of cells.

Preferable ranges of "biocompatible polymer blocks (types, sizes, or the like)", "cells", "gaps between cells", "obtained cell structures (sizes or the like)", "a ratio of cells and polymer blocks", and the like in the method of manufacturing the cell structure used in the present invention are the same as those of the present specification.

(5) Trophic Factor Releasing Agent

According to the trophic factor releasing agent of the embodiment of the present invention, trophic factors are released from cells of a cell structure. The release of the trophic factor from the cell means that trophic factors are produced in cells, and the trophic factors produced in the cells are secreted to the outside of the cells.

A trophic factor means a substance having physiological activity or biological activity (particularly, a material produced by a cell). Examples of the trophic factor include cytokine, a hormone, a proliferation factor, and enzyme.

Cytokine means a proteinaceous factor released from a cell and mediating cell-cell interaction.

A hormone is a chemical material that is produced in an animal body (generally an endocrine gland), is secreted into a body fluid, and gives a constant change in the activity of a specific organ, a tissue, a cell, or the like.

A proliferation factor means a material that promotes or controls cell proliferation.

An enzyme means protein that catalyzes various chemical reactions in vivo.

Cytokine, a hormone, a proliferation factor, and an enzyme do not have mutually exclusive meanings.

Specific examples of the trophic factor include TNF-stimulated gene 6 protein (TSG-6) (TNF is a Tumor Necrosis Factor), angiogenin (ANG), an epidermal growth factor (EGF), epithelial derived neutrophil-activating peptide 78 (ENA-78), a basic fibroblast growth factor (bFGF), an insulin-like growth factor (IGF) (such as IGF-1), membrane cofactor protein (MCP) (such as MCP-1), a platelet derived growth factor (PDGF) (such as PDGF-BB), a transforming growth factor (TGF) (such as TGFβ), tissue inhibitors of matrix metalloproteinase (TIMP) (such as TIMP-1 and TIMP-2), thrombopoietin (THPO), a vascular endothelial growth factor (VEGF), a vascular endothelial growth factor D (VEGF-D), a nerve growth factor (NGF), a brain derived neurotrophic factor (BDNF), a granulocyte-colony stimulating factor (G-CSF), a granulocyte macrophage colony-stimulating factor (GM-CSF), Erythropoietin (EPO), Thrombopoietin (TPO), a hepatocyte growth factor (HGF), bone morphogenetic protein (BMP), a fibroblast growth factor (FGF), INTERLEUKIN (such as Interleukin-6 (IL-6) and Interleukin-8 (IL-8)), chemokine, Interferon (such as interferon gamma (IFNγ)), a tumor necrosis factor (TNF), adipokine, inhibin, a parathyroid hormone, calcitonin, a thyrotropin releasing hormone, a thyroid stimulating hormone, vasopressin, an adrenocorticotropin releasing hormone, an adrenocorticotropic hormone, a gonadotropin-releasing hormone, a gonadotropic hormone, proolactin, melatonin, oxytocin, insulin, glucagon, somatostatin, a growth hormone releasing hormone, a growth hormone, a thyroid hormone, thyroxine, an adrenal medullary hormone, adrenaline, noradrenaline, androgen, testosterone, estrogen, progesterone, aldosterone, and cortisol.

The trophic factor is preferably one or more of TSG-6, ANG, EGF, ENA-78, bFGF, IFNγ, IGF-1, IL-6, IL-8, MCP-1, PDGF-BB, TGFβ, TIMP-1, TIMP-2, THPO, VEGF, and VEGF-D.

The trophic factor is more preferably one or more of TSG-6, ANG, EGF, ENA-78, IGF-1, IL-8, PDGF-BB, TGFβ, THPO, and VEGF-D.

The trophic factor is particularly preferably TSG-6.

According to another aspect, the trophic factor is preferably cytokine, more preferably anti-inflammatory cytokine, and particularly preferably TSG-6.

The anti-inflammatory cytokine means cytokine having an anti-inflammatory effect. Examples of the anti-inflammatory cytokine include TSG-6, TGFβ, IL-4, IL-5, IL-6, IL-10, IL-13, IL-14, IL-22, IL-27, IL-33, IL-37, IL-38, Interleukin-1 Receptor Antagonist (IL-1ra), Fas ligand (FasL), TNF-related apotosis-inducing ligand (TRAIL), Type I interferon (Interferon alfa (IFNα) and Interferon beta (IFNβ)), Human leukocyte-type antigen-G5 (HLA-G5 (human leukocyte antigen G5), indoleamine-2,3-dioxigenase (IDO), and Prostaglandin E2 (PGE2)).

As the trophic factor, a ratio of a production release amount in a cell mass to a production release amount in a mosaic cell mass is preferably 1.1 times or more, more preferably 1.2 times or more, even more preferably 1.3 times or more, and particularly preferably 1.4 times or more.

The production release amount can be measured by respectively culturing a mosaic cell mass and a cell mass and quantifying an amount of trophic factors released to a culture supernatant after 3 days. The quantifying of the trophic factor amount can be performed by a general method by a well-known method with a commercially available kit according to the types of the trophic factors.

The trophic factor releasing agent of the embodiment of the present invention can be transplanted into a living body to be used. As the transplantation method, it is possible to use incision, injection, and a method using an endoscope. The trophic factor releasing agent of the embodiment of the present invention can reduce the size of the structure unlike a cellular implant such as a cell sheet, and thus a minimally invasive transplantation method such as transplantation by injection becomes possible.

The amount at which the trophic factor releasing agent of the embodiment of the present invention is transplanted can be appropriately selected according to the state of the transplant subject or the like, but the number of transplanted cells is preferably $1.0 \times 10^5$ cells/kg to $2.0 \times 10^9$ cells/kg and more preferably $1.0 \times 10^6$ cells/kg to $2.0 \times 10^8$ cells/kg.

With respect to the number of transplantation of the trophic factor releasing agent of the embodiment of the present invention, the transplantation may be performed once or the transplantation may be performed twice or more, if necessary.

(6) Inflammatory Disease Treating Agent

As understood from the result of the TSG-6 production release amount test dependent on inflammation stimulated TNFα presented in Example 12 below, in the trophic factor releasing agent of the embodiment of the present invention, compared with a case where the stimulation is not performed in TNFα, prominent TSG-6 production and release by performing TNFα stimulation have been recognized. That is, the trophic factor releasing agent of the embodiment of the present invention has high responsiveness to inflammatory stimuli and can release a large amount of anti-inflammatory cytokine and thus is useful as an agent for treating inflammatory diseases. According to the present invention, provided is an inflammatory disease treating agent including the trophic factor releasing agent of the embodiment of the present invention.

As presented in the following examples, the cell structure that includes the biocompatible polymer blocks and the mesenchymal stem cells and in which the plurality of biocompatible polymer blocks are disposed in gaps between the plurality of mesenchymal stem cells can exhibit an inflammatory disease treatment effect. It is considered that the inflammatory disease treating agent of the embodiment of the present invention exhibits an inflammatory disease treatment effect by releasing anti-inflammatory cytokine and suppressing proliferation or activation of T cells.

An inflammatory disease is a disease that expresses a disease state by the presence of an inflammatory reaction in a living body.

Examples of the inflammatory diseases include inflammatory bowel disease, ulcerative colitis, crohn's disease, nephritis, acute nephritis, chronic nephritis, glomerulonephritis, iga nephropathy, diabetic nephropathy, membranous nephropathy, hydronephrosis, contrast agent nephropathy, pyelonephritis, kidney failure, acute nephritis, chronic nephritis, interstitial nephritis, renal disorder, nephrotic syndrome, hypertensive nephrosclerosis, diabetic glomerulosclerosis, kidney stone, amyloid kidney, renal vein thrombosis, alport syndrome, hepatitis, cirrhosis of the liver, pancreatitis, pneumonia, sinusitis, rhinitis, arthritis, rheumatoid arthritis, periodic fever•aphthous stomatitis•pharyngitis•lymphadenitis syndrome (PFAPA), adult onset still's disease, behcet's disease, gout, pseudogout, schnitzler syndrome, chronic recurrent multiple osteomyelitis (CRMO), cryopyrine related periodic fever syndrome (CAPS), familial cold urticaria, muckle-wells syndrome, chronic infantile neurodermal arthritis syndrome (CINCA syndrome)/neonatal onset multiple organ inflammatory disease (NOMID), tumor necrosis factor (TNF) receptor related periodic syndrome (TRAPS), High IgD syndrome (mevalonate kinase deficiency), Blau syndrome/juvenile onset sarcoidosis, familial Mediterranean fever, purulent arthritis/pyoderma gangrenosum/acne syndrome (PAPA), Nakajo-Nishimura syndrome, majeed syndrome, NLRP 12 related periodic fever syndrome (NAPS 12), Interleukin 1 receptor antagonist deficiency (DIRA), Interleukin 36 receptor antagonist deficiency (DITRA), phospholipase Cγ2-related antibody deficiency/immune disorder (PLAID), HOIL-1 deficiency, SLC29A3 deficiency, CARD 14 abnormality disease, adenosine deaminase 2 (ADA2) deficiency, STING-associated vasculopathy with onset in infancy (SAVI), and NLRC4 abnormality, and an inflammatory bowel disease is preferable.

The treatment means prevention or treatment of various diseases and the like.

The prevention means preliminarily suppressing the progress of symptoms specific to the disease of interest, and includes inhibition of onset, reduction in the risk of onset, or delay of onset. The extent of suppression of progression is not limited at all and even if the extent is very small, as long as the progression can be suppressed, the suppression is included in prevention.

The treatment means improvement or suppression of progression on the disease or state of interest.

The treating agent means a material provided for the purpose of the treatment.

The inflammatory disease treating agent of the embodiment of the present invention can be transplanted into a living body to be used. As the transplantation method, it is possible to use incision, injection, and a method using an endoscope. The inflammatory disease treating agent of the embodiment of the present invention can reduce the size of the structure unlike a cellular implant such as a cell sheet, and thus a minimally invasive transplantation method such as transplantation by injection becomes possible.

The amount at which the inflammatory disease treating agent of the embodiment of the present invention is transplanted can be appropriately selected according to the state of the transplant subject or the like, but the number of transplanted cells is preferably $1.0 \times 10^5$ cells/kg to $2.0 \times 10^9$ cells/kg and more preferably $1.0 \times 10^6$ cells/kg to $2.0 \times 10^8$ cells/kg. With respect to the number of transplantation of the inflammatory disease treating agent of the embodiment of the present invention, the transplantation may be performed once or the transplantation may be performed twice or more, if necessary.

(7) Various Applications

According to the present invention, there is provided a method of releasing a trophic factor including the step of transplanting a cell structure defined in the present invention to a subject in need of a trophic factor. According to the present invention, there is provided a method of treating an inflammatory disease including the step of transplanting a cell structure defined in the present invention to a subject in need of treatment of an inflammatory disease. In the above method, the preferable ranges of the cell structure and the trophic factor are the same as described above.

According to the present invention, there is provided a cell structure defined in the present invention for the treatment for trophic factor release and/or by trophic factor release. According to the present invention, there is provided a cell structure defined in the present invention for the treatment of inflammatory disease. In the cell structure, the preferable range of the cell structure and the trophic factor is the same as described above.

According to the present invention, there is provided the use of a cell structure defined in the present invention for manufacturing a trophic factor releasing agent. According to the present invention, there is provided the use of the cell structure defined in the present invention for manufacturing inflammatory disease treating agent. In the above use, the preferable range of the cell structure and the trophic factor is the same as described above.

The present invention will be more specifically described using the following examples, but is not limited by the examples.

EXAMPLES

Example 1

Recombinant Peptide (Recombinant Gelatin)

The following CBE3 (which is disclosed in WO2008/103041A) was prepared as recombinant peptides (recombinant gelatin).

CBE3:
Molecular weight: 51.6 kDa
Structure: GAP[(GXY)$_{63}$]$_3$G
Number of amino acids: 571
RGD sequence: 12
Imino acid content: 33%
Almost 100% of amino acids have a repeating structure of GXY. In the amino acid sequence of CBE3, serine, threonine, asparagine, tyrosine, and cysteine are not included. CBE3 has an ERGD sequence.
Isoelectric point: 9.34
GRAVY value: −0.682
1/IOB value: 0.323
Amino acid sequence (SEQ ID No: 1 in a sequence table) (which is the same as that of SEQ ID No: 3 in WO2008/103041A. However, X in the end is corrected to "P").

GAP(GAPGLQGAPGLQGMPGERGAAGLPGPKGERGDAGPKGADGAPGAPG

LQGMPGERGAAGLPGPKGERGDAGPKGADGAPGKDGVRGLAGPIGPPGER

GAAGLPGPKGERGDAGPKGADGAPGKDGVRGLAGPIGPPGPAGAPGAPGL

QGMPGERGAAGLPGPKGERGDAGPKGADGAPGKDGVRGLAGPP)$_3$G

[Example 2] Production of Porous Body of Recombinant Peptide

[PTFE Thickness•Cylindrical Container]

A cylindrical cup-shaped polytetrafluoroethylene (PTFE) container with a bottom surface thickness of 3 mm, a diameter of 51 mm, a side surface thickness of 8 mm, and a height of 25 mm was prepared. In a case where the curved surface of the cylindrical cup is set as a side surface, the side surface is closed by PTFE with 8 mm and the bottom surface (circular shape of a flat plate) is also closed by PTFE with 3 mm. In contrast, the upper surface is in an open shape. Accordingly, the inner diameter of the cylindrical cup is set to 43 mm. Hereinafter, this container is referred to as a PTFE thickness•cylindrical container.

[Aluminum Glass Plate•Cylindrical Container]

A cylindrical cup-shaped aluminum container with a thickness of 1 mm and a diameter of 47 mm was prepared. In a case where the curved surface of the cylindrical cup is set as a side surface, the side surface is closed by aluminum with 1 mm and the bottom surface (circular shape of a flat plate) is also closed by aluminum with 1 mm. In contrast, the upper surface is in an open shape. In addition, TEFLON (registered trademark) with a thickness of 1 mm is evenly spread only in the inside of the side surface, and as a result, the inner diameter of the cylindrical cup becomes 45 mm. In addition, the bottom surface of this container enters a state where a 2.2 mm glass plate is joined to the bottom surface thereof on the outside of aluminum. Hereinafter, this container is referred to as an aluminum glass•cylindrical container.

[Freezing Step in which Difference in Temperature is Small, and Drying Step]

An aqueous CBE3 solution was made to flow into the PTFE thickness•cylindrical container and the aluminum glass plate•cylindrical container, and was cooled down from the bottom surface within a vacuum freeze dryer (TF5-85ATNNN: Takara Co., Ltd.) using a cooling shelf. A combination of the setting of the final concentration of the aqueous CBE3 solutions in the containers at this time, the amount of solution, and the temperature of the shelf was prepared as described below.

Condition A:

PTFE thickness•cylindrical container, final concentration of aqueous CBE3 solution of 4 mass %, amount of aqueous solution of 4 mL. As the setting for the temperature of the shelf, the temperature was cooled down until the temperature reaches −10° C., and then, freezing was performed for 1 hour at −10° C., for 2 hours at −20° C., for 3 hours at −40° C., and finally for 1 hour at −50° C. Thereafter, the frozen product was subjected to vacuum drying for 24 hours at −20° C. after the setting of the temperature of the shelf was returned to −20° C. After 24 hours, the temperature of the shelf was increased to 20° C. in a state in which the vacuum drying was continued as it was, and the vacuum drying was further performed for 48 hours at 20° C. until the vacuum degree was sufficiently decreased ($1.9 \times 10^5$ Pa). Then, the product was taken out of the vacuum freeze dryer. As described above, a porous body was obtained.

Condition B:

Aluminum•glass•plate•cylindrical container, final concentration of aqueous CBE3 solution of 4 mass %, amount of aqueous solution of 4 mL. As the setting for the temperature of the shelf, the temperature was cooled down until the temperature reaches −10° C., and then, freezing was performed for 1 hour at −10° C., for 2 hours at −20° C., for 3 hours at −40° C., and finally for 1 hour at −50° C. Thereafter, the frozen product was subjected to vacuum drying for 24 hours at −20° C. after the setting of the temperature of the shelf was returned to −20° C. After 24 hours, the temperature of the shelf was increased to 20° C. in a state in which the vacuum drying was continued as it was, and the vacuum drying was further performed for 48 hours at 20° C. until the vacuum degree was sufficiently decreased ($1.9 \times 10^5$ Pa). Then, the product was taken out of the vacuum freeze dryer. As described above, a porous body was obtained.

Condition C:

PTFE thickness•cylindrical container, final concentration of aqueous CBE3 solution of 4 mass %, amount of aqueous solution of 10 mL. As the setting for the temperature of the shelf, the temperature was cooled down until the temperature reaches −10° C., and then, freezing was performed for 1 hour at −10° C., for 2 hours at −20° C., for 3 hours at −40° C., and finally for 1 hour at −50° C. Thereafter, the frozen product was subjected to vacuum drying for 24 hours at −20° C. after the setting of the temperature of the shelf was returned to −20° C. After 24 hours, the temperature of the shelf was increased to 20° C. in a state in which the vacuum drying was continued as it was, and the vacuum drying was further performed for 48 hours at 20° C. until the vacuum degree was sufficiently decreased ($1.9 \times 10^5$ Pa). Then, the product was taken out of the vacuum freeze dryer. As described above, a porous body was obtained.

[Measurement of Temperature in Each Freezing Step]

Regarding the conditions A to C, the liquid temperature of the surface of water in a center portion of a circle within a container was measured as the liquid temperature (non-cooled surface liquid temperature) of the farthest portion from a cooling side in a solution, and the liquid temperature of a bottom portion within the container was measured as the liquid temperature (cooled surface liquid temperature) of the closest portion to the cooling side in the solution.

Figure 3:
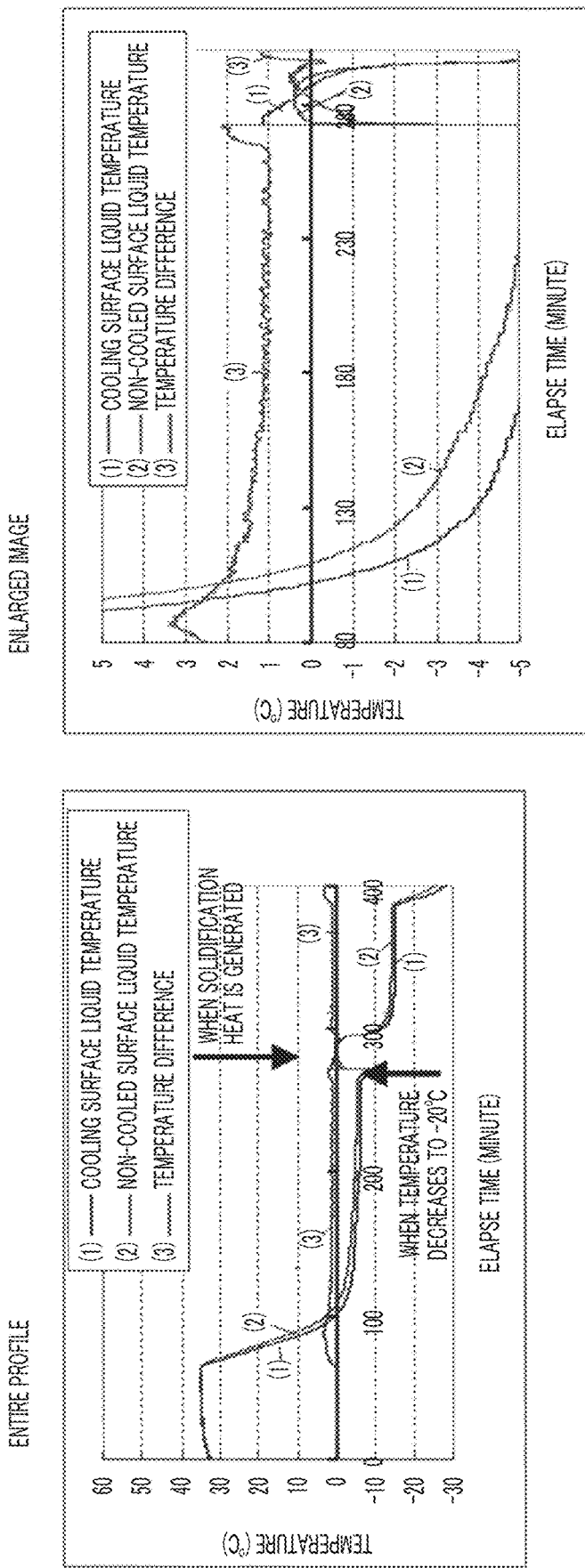
FIG. 3 illustrates liquid temperature profiling of an experiment described in Condition C.

As a result, each temperature and a profile of the difference in temperature are as shown in FIGS. 1 to 3.

It can be seen from FIGS. 1 to 3 that the liquid temperature falls below 0° C., which is a melting point, in a setting section of the temperature of a shelf of −10° C. (before the temperature decreases to −20° C.) in the conditions A to C, and the solution enters a (unfrozen and overcooled) state where freezing does not occur in that state. In addition, in this state, the difference in temperature between the cooled surface liquid temperature and the non-cooled surface liquid temperature is less than or equal to 2.5° C. In the present specification, the "difference in temperature" means "non-cooled surface liquid temperature"–"cooled surface liquid temperature". Thereafter, the timing at which the liquid temperature rapidly rises to around 0° C. by further lowering the temperature of the shelf to −20° C. is confirmed. Here, it can be seen that freezing starts due to generation of solidification heat. In addition, it was also possible to confirm that ice formation actually started at the timing. Thereafter, the temperature was around 0° C. while the certain time passes. Here, the product entered a state where there was a mixture of water and ice. The temperature finally started to decrease again from 0° C. Accordingly, the temperature being measured became a solid temperature within the ice, that is, was not the liquid temperature.

Hereinafter, regarding the conditions A to C, the difference in temperature at this time when the non-cooled surface liquid temperature became a melting point (0° C.), the difference in temperature immediately before the temperature of the shelf is decreased from −10° C. to −20° C., and the difference in temperature immediately before the generation of solidification heat will be described. The "difference in temperature immediately before" referred in the present invention indicates the highest temperature in the difference in temperature which can be detected between 1 second to 20 seconds before an event (such as the generation of solidification heat).

Condition A:

Difference in temperature at this time when non-cooled surface liquid temperature became melting point (0° C.): 1.1° C.

Difference in temperature immediately before temperature is decreased from −10° C. to −20° C.: 0.2° C.

Difference in temperature immediately before generation of solidification heat: 1.1° C.

Condition B:

Difference in temperature at this time when non-cooled surface liquid temperature became melting point (0° C.): 1.0° C.

Difference in temperature immediately before temperature is decreased from −10° C. to −20° C.: 0.1° C.

Difference in temperature immediately before generation of solidification heat: 0.9° C.

Condition C:

Difference in temperature at this time when non-cooled surface liquid temperature became melting point (0° C.): 1.8° C.

Difference in temperature immediately before temperature is decreased from −10° C. to −20° C.: 1.1° C.

Difference in temperature immediately before generation of solidification heat: 2.1° C.

[Example 3] Production of Biocompatible Polymer Block (Pulverizing and Cross-Linking of Porous Body)

The CBE3 porous bodies of Conditions A and B which had been obtained in Example 2 were pulverized using NEW POWERMILL (Osaka Chemical Co., Ltd., NEW POWERMILL PM-2005). The pulverizing was performed for one minute×5 times, that is, for 5 minutes in total at the maximum rotation speed. The sizes of the obtained pulverized substances were divided using a stainless steel sieve to obtain uncross-linked blocks with 25 to 53 μm, 53 to 106 μm, and 106 to 180 μm. Thereafter, biocompatible polymer blocks (CBE3 blocks) were obtained by performing thermal cross-linking (six kinds of cross-linking times of 8 hours, 16 hours, 24 hours, 48 hours, 72 hours, and 96 hours) at 160° C. under reduced pressure.

Hereinafter, a porous body derived block under the condition A which has been cross-linked for 48 hours is called E, and a porous body derived block under the condition B which has been cross-linked for 48 hours is called F. E and F are blocks with a small difference in temperature which have been produced from porous bodies produced through a freezing step in which the difference in temperature is small. There was no influence of the difference in cross-linking time on the performance in the evaluation of the present examples. Therefore, the blocks cross-linked for 48 hours were representatively used. There was no difference in performance between E and F. In examples, biocompatible polymer blocks which have sizes of 53 to 106 μm, are produced under the condition A, and of which the cross-linking time is 48 hours were used.

[Example 4] Measurement of Tap Density of Biocompatible Polymer Block

The tap density is a value indicating how much volume of block can be densely filled. It can be said that, as the value becomes smaller, the block cannot be densely filled, that is, the structure of the block is complicated. The tap density was measured as follows. First, a funnel with an attached cap (having a cylindrical shape with a diameter of 6 mm and a length of 21.8 mm: capacity of 0.616 cm$^3$) at the tip thereof was prepared, and the mass of only the cap was measured. Thereafter, the cap was attached to the funnel, and blocks were poured from the funnel so as to be collected in the cap. After placing a sufficient amount of block, the cap portion was hit 200 times on a hard object such as a desk, the funnel was removed, and the blocks were leveled with a spatula. The mass was measured in a state where the cap was filled up with the blocks. The tap density was obtained by calculating the mass of only the blocks from the difference between the mass of the cap filled up with the blocks and the mass of only the cap, and dividing the mass of only the blocks by the volume of the cap.

As a result, the tap density of the biocompatible polymer blocks of Example 3 was 98 mg/cm$^3$.

[Example 5] Measurement of Cross-Linking Degree of Biocompatible Polymer Block

The cross-linking degree (the number of cross-linking times per molecule) of the blocks cross-linked in Example 3 was calculated. The measurement was performed through a TNBS (2,4,6-trinitrobenzene sulfonic acid) method.
<Preparation of Sample>
A sample (about 10 mg), 4 mass % NaHCO$_3$ aqueous solution (1 mL), and 1 mass % TNBS aqueous solution (2 mL) were added to a glass vial, and the mixture was shaken for 3 hours at 37° C. Thereafter, 37 mass % hydrochloric acid (10 mL) and pure water (5 mL) were added thereto, and then, the mixture was allowed to stand for 16 hours or longer at 37° C. to prepare a sample.
<Preparation of Blank>
A sample (about 10 mg), 4 mass % NaHCO$_3$ aqueous solution (1 mL), and 1 mass % TNBS aqueous solution (2 mL) were added to a glass vial, 37 mass % hydrochloric acid (3 mL) was immediately added thereto, and the mixture was shaken for 3 hours at 37° C. Thereafter, 37 mass % hydrochloric acid (7 mL) and pure water (5 mL) were added thereto, and then, the mixture was allowed to stand for 16 hours or longer at 37° C. to prepare a blank.

The absorbance (345 nm) of the sample and the blank which had been diluted 10 times with pure water was measured, and the cross-linking degree (the number of cross-linking times per molecule) was calculated from (Formula 2) and (Formula 3).

$$(As-Ab)/14,600 \times V/w \quad \text{(Formula 2)}$$

(Formula 2) represents the amount (molar equivalent) of lysine per 1 g of recombinant peptide.
(in the formula, As represents the sample absorbance, Ab represents the blank absorbance, V represents the amount (g) of reaction liquid, and w represents the mass (mg) of recombinant peptide.)

$$1-(\text{sample (Formula 2)/uncross-linked recombinant peptide (Formula 2)}) \times 34 \quad \text{(Formula 3)}$$

(Formula 3) represents the number of cross-linking times per molecule.

As a result, the cross-linking degree of the biocompatible polymer blocks of Example 3 was 4.2.

[Example 6] Measurement of Water Absorption Rate of Biocompatible Polymer Block

The water absorption rate of biocompatible polymer blocks produced in Example 3 was calculated.

A 3 cm×3 cm nylon mesh bag was filled with about 15 mg of the biocompatible polymer blocks at 25° C. and was swollen in ion exchange water for 2 hours. Then, the biocompatible polymer blocks were dried with air for 10 minutes, and the mass was measured at each stage to obtain the water absorption rate according to (Formula 4).

$$\text{Water absorption rate}=(w2-w1-w0)/w0 \quad \text{(Formula 4)}$$

(in the formula, w0 represents the mass of a material before water absorption, w1 represents the mass of an empty bag after water absorption, and w2 represents the mass of the entirety of the bag containing the material after water absorption.)

As a result, the water absorption rate of the blocks of Example 3 was 786%.

[Example 7] Manufacturing of Mosaic Cell Mass

Human bone marrow derived mesenchymal stem cells (hMSCs: Human Mesenchymal Stem Cells) were suspended in a proliferation medium (Takara Bio Inc.: MSCGM Bullet Kit (trademark)), and biocompatible polymer blocks (53 to 106 μm) manufactured in Example 3 were added thereto. The mixture was sown in EZSPHERE (registered trademark) DISH 35 mm Type 903 (which had a spheroid well diameter of 800 μm, a spheroid well depth of 300 μm, and several spheroid wells to about 1,000 wells, and was manufactured by AGC TECHNO GLASS CO., Ltd.) which was a cell non-adhesive 35 mm dish having recessed portions on the bottom surface thereof, in a state in which hMSCs (1.2×10$^6$ cells) and biocompatible polymer blocks (1 mg) were finally suspended in 4 mL of a medium.

The dish was allowed to stand in a CO$_2$ incubator at 37° C. for 20 hours, and it was possible to collect a plurality of mosaic cell masses in a spherical shape which has a diameter of about 0.4 mm and is formed of hMSCs and biocompatible polymer blocks.

It was confirmed that, in a case where any one of Type 900 (with a well diameter of 400 to 500 μm and a well depth of 100 to 200 μm), Type 902 (with a well diameter of 500 μm and a well depth of 200 μm), Type 904 (with a well diameter of 800 μm and a well depth of 400 μm), or Type 905 (with a well diameter of 1,400 μm and a well depth of 600 μm) was used as a dish, it was possible to obtain a spherical mosaic cell mass as described above.

[Comparative Example 1] Manufacturing of Cell Mass of Cell Only

Human bone marrow derived mesenchymal stem cells (hMSCs) were suspended in a proliferation medium (Takara Bio Inc.: MSCGM Bullet Kit (trademark)). The mixture was sown in EZSPHERE (registered trademark) DISH 35 mm Type 903 (which had a spheroid well diameter of 800 μm, a spheroid well depth of 300 μm, and several spheroid wells to about 1,000 wells, and was manufactured by AGC TECHNO GLASS CO., Ltd.) which was a cell non-adhesive 35 mm dish having recessed portions on the bottom surface thereof, in a state in which hMSCs ($1.2 \times 10^6$ cells) were finally suspended in 4 mL of a medium.

The dish was allowed to stand in a $CO_2$ incubator at 37° C. for 20 hours, and as a result, it was possible to collect a plurality of cell masses that are formed of hMSCs only.

[Example 8] Measuring of Release Amount of Trophic Factors

The mosaic cell mass of Example 7 and the cell mass of Comparative Example 1 were respectively cultured, and amounts of trophic factors released to culture supernatants were measured after three days. In the measurement, a kit of Human Angiogenesis Antibody Array C1 (#AAH-ANG-1-8, RayBio) was used. As a result, it was found that the amount of the trophic factors released from the mosaic cell mass was greater than the release amount from the cell mass. Specifically, it was found that ANG was increased by 1.74 times, EGF was increased by 1.92 times, ENA-78 was increased by 2.22 times, bFGF was increased by 1.09 times, IFNγ was increased by 1.11 times, IGF-1 was increased by 1.44 times, IL-6 was increased by 1.37 times, IL-8 was increased by 1.86 times, MCP-1 was increased by 1.29 times, PDGF-BB was increased by 3.60 times, TGFβ was increased by 1.40 times, TIMP-1 was increased by 1.13 times, TIMP-2 was increased by 1.33 times, THPO was increased by 1.43 times, VEGF was increased by 1.37 times, and VEGF-D was increased by 2.54 times, by using mosaic cell masses. From the above results, by using the mosaic cell masses, it has been clearly found that the production release amount of the trophic factors increased (Table 1).

[Example 9] Manufacturing of Mosaic Cell Masses (hMSC)

Human bone marrow derived mesenchymal stem cells (hMSC) were adjusted to 100,000 cells/mL in a Dulbecco's modified eagle medium (DMEM)+a 10% fetal bovine serum (FBS) medium, biocompatible polymer block 53-106 μm manufactured in Example 3 was added to be 0.1 mg/mL, 200 μL was seeded on a Sumilon Celtite X96U plate (Sumitomo Bakelite Company Limited, a bottom has a U shape), centrifugation (600 g, 5 minutes) was performed on a tabletop plate centrifuge, and the resultant was allowed to stand for 24 hours, so as to manufacture a spherical mosaic cell mass consisting of biocompatible polymer blocks and hMSC cells having a diameter of 1 mm (0.001 μg block per cell). Since the mosaic cell mass was manufactured in a U-shaped plate, this mosaic cell mass was spherical.

[Example 10] Manufacturing of Mosaic Cell Mass (hADSC)

Human adipose derived stem cells (HADSC) were adjusted to 100,000 cells/mL in DMEM+a 10% FBS medium, biocompatible polymer block 53-106 μm manufactured in Example 3 was added to be 0.1 mg/mL, 200 μL was seeded on a Sumilon Celtite X96U plate (Sumitomo Bakelite Company Limited, a bottom has a U shape), centrifugation (600 g, 5 minutes) was performed on a tabletop plate centrifuge, and the resultant was allowed to stand for 24 hours, so as to manufacture a spherical mosaic cell mass consisting of biocompatible polymer blocks and hADSC cells having a diameter of 1 mm (0.001 μg block per cell). Since the mosaic cell mass was manufactured in a U-shaped plate, this mosaic cell mass was spherical.

[Comparative Example 2] Manufacturing of Cell Mass (hMSC)

Human bone marrow derived mesenchymal stem cells (hMSC) were adjusted to 100,000 cells/mL in DMEM+a 10% FBS medium, 200 μL was seeded on a Sumilon Celtite X96U plate (Sumitomo Bakelite Company Limited, a bottom has a U shape), centrifugation (600 g, 5 minutes) was performed on a tabletop plate centrifuge, and the resultant was allowed to stand for 24 hours, so as to manufacture a cell mass consisting of hMSC cells only. Since the mosaic cell mass was manufactured in a U-shaped plate, this cell mass was spherical.

TABLE 1

| | Name of trophic factor | | | | | | | |
|---|---|---|---|---|---|---|---|---|
| | ANG | EGF | ENA-78 | bFGF | IFNγ | IGF-1 | IL-6 | IL-8 |
| Ratio of release amount (mosaic cell mass/cell mass) | 1.74 | 1.92 | 2.22 | 1.09 | 1.11 | 1.44 | 1.37 | 1.86 |

| | Name of trophic factor | | | | | | | |
|---|---|---|---|---|---|---|---|---|
| | MCP-1 | PDGF-BB | TGFβ | TIMP-1 | TIMP-2 | THPO | VEGF | VEGF-D |
| Ratio of release amount (mosaic cell mass/cell mass) | 1.29 | 3.60 | 1.40 | 1.13 | 1.33 | 1.43 | 1.37 | 2.54 |

[Comparative Example 3] Manufacturing of Cell Mass (hADSC)

Human adipose derived stem cells (hADSC) were adjusted to 100,000 cells/mL in DMEM+a 10% FBS medium, 200 μl, was seeded on a Sumilon Celtite X96U plate (Sumitomo Bakelite Company Limited, a bottom has a U shape), centrifugation (600 g, 5 minutes) was performed on a tabletop plate centrifuge, and the resultant was allowed to stand for 24 hours, so as to manufacture a cell mass consisting of hADSC cells only. Since the mosaic cell mass was manufactured in a U-shaped plate, this cell mass was spherical.

[Example 11] Release Amount Test of Anti-Inflammatory Cytokine TSG-6

The mosaic cell masses obtained in Examples 9 and 10 and the cell masses obtained in Comparative Example 2 and 3 were respectively cultured, and TSG-6 released to culture supernatants was quantified after three days. In the quantification, RayBio Human TSG-6 ELISA Kit (cat #: ELH-TSG6 (manufactured by RayBiotech, Inc.)) was used.

Figure 4:
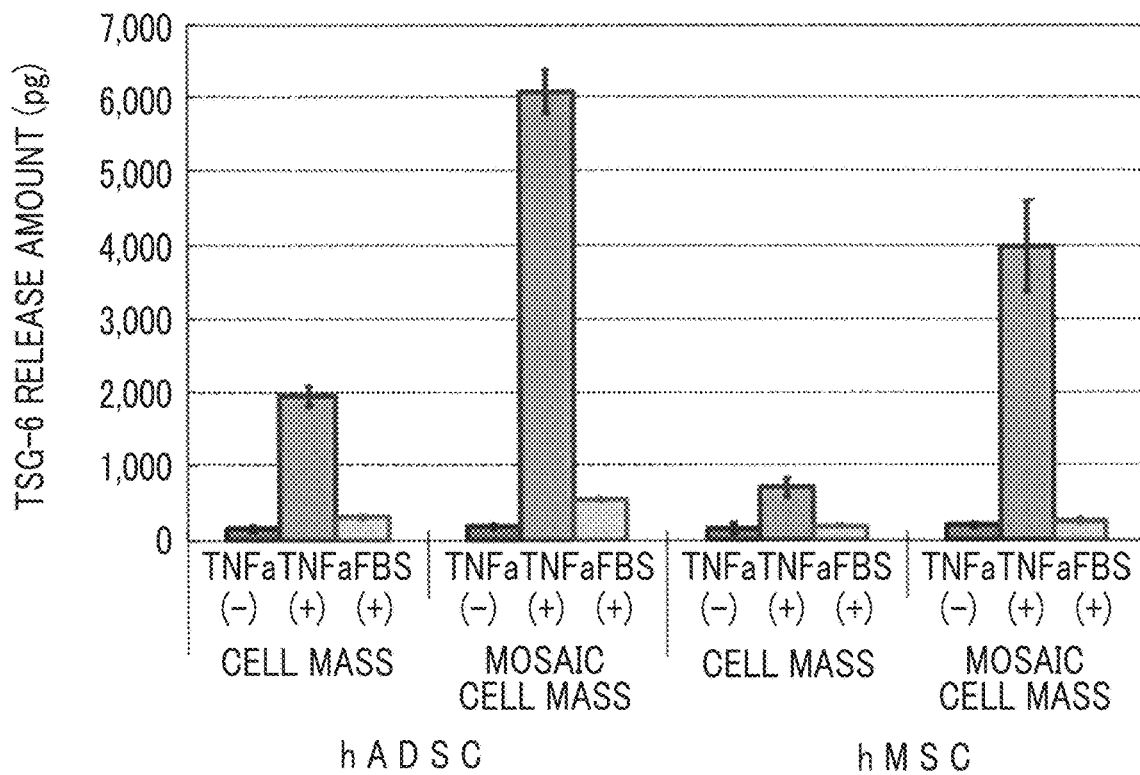
FIG. 4 illustrates results obtained by measuring a TSG-6 production release amount dependent on inflammation stimulated TNFα.

The result of quantifying TSG-6 was illustrated in FIG. 4 (see the section of FBS(+)). As a result, it was found that a release amount of the mosaic cell mass in hMSC was greater than that of the cell mass by 1.4 times, and a release amount of the mosaic cell masses in hADSC was greater than that of the cell mass by 1.8 times. Accordingly, it was clearly found that, in TSG-6, production release amount increased by using a mosaic cell mass.

[Example 12] TSG-6 Production Release Amount Test Dependent on Inflammation Stimulated Tumor Necrosis Factor α (TNFα)

The mosaic cell masses obtained in Examples 9 and 10 and the cell masses obtained in Comparative Examples 2 and 3 were substituted with the DMEM medium not including FBS, then culturing was performed for 48 hours in a TNFα-containing DMEM medium, and TSG-6 released to a culture supernatant was quantified. In the quantification, RayBio Human TSG-6 ELISA Kit (cat #: ELH-TSG6 (RayBiotech, Inc.)) was used.

The result of the quantification of TSG-6 was illustrated in FIG. 4 (see the section of TNFα(+)).

As a result, it was found that a release amount of the mosaic cell mass in hMSC was greater than that of the cell mass by 5.7 times, and a release amount of the mosaic cell masses in hADSC was greater than that of the cell mass by 3.1 times. Compared with a case where the stimulation is not performed in TNFα, prominent TSG-6 production and release by performing TNFα stimulation have been recognized (see FIG. 4: the section of TNFα(−) and TNFα(+)).

Figure 5:
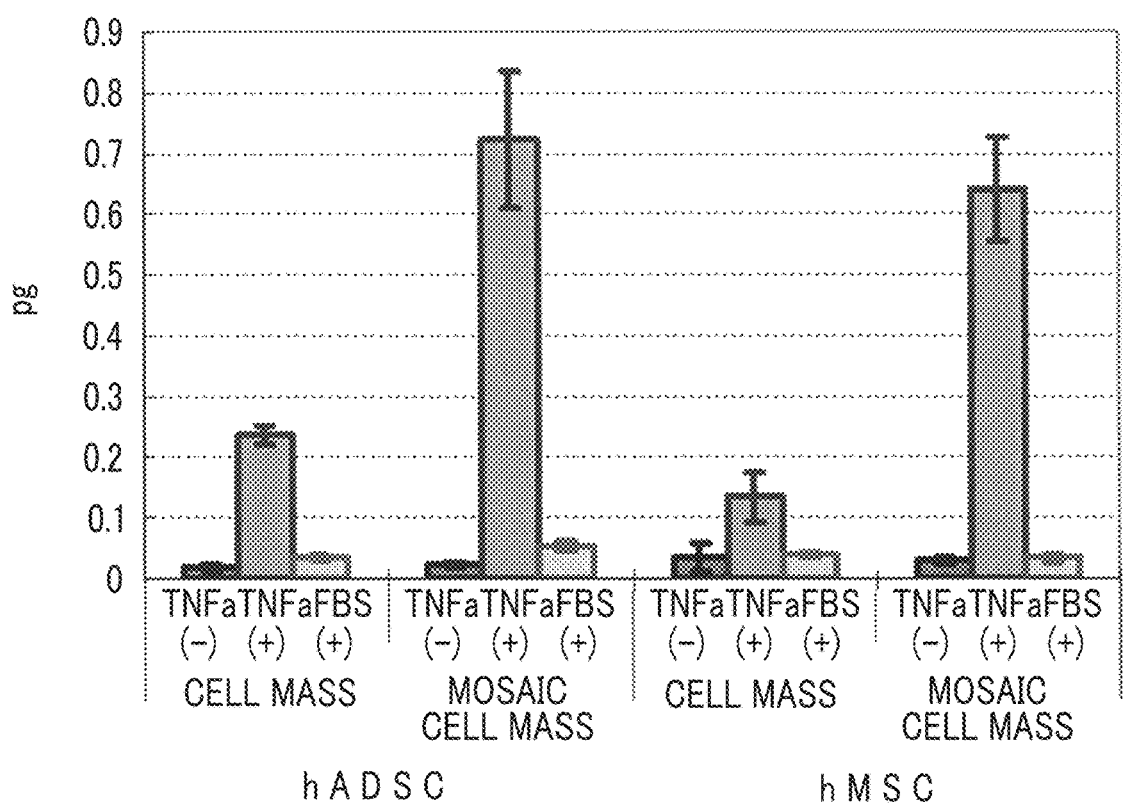
FIG. 5 illustrates results of TSG-6 production release amounts dependent on inflammation stimulated TNFα which are obtained as a production release amount per one cell.

The same effect was recognized in the production release amount per cell which was obtained by dividing the release amount with the number of viable cells (FIG. 5).

It is well-known that the TNFα stimulation promotes the TSG-6 production, but with respect to the responsiveness to the TNFα stimulation, it was completely unexpected that responsiveness dramatically increased in a case of using the mosaic cell mass. Accordingly, with respect to TSG-6, it was clearly found that, by using the mosaic cell mass, not only the production release amount increased, but also the responsiveness to the TNFα stimulation increased. This indicates that the mosaic cell mass is highly responsive to inflammatory stimulation and releases a large amount of anti-inflammatory cytokine, and thus the mosaic cell mass is very useful as an anti-inflammatory treating agent.

[Example 13] Manufacturing of Mosaic Cell Mass (hADSC)

Human adipose derived stem cells (hADSC) were suspended in a proliferation medium (Lonza: ADSC-BulletKit (Trademark), hereinafter, also referred to as an ADSC medium), biocompatible polymer blocks (53 to 106 μm) manufactured in Example 3 were added and sown in EZSPHERE (registered trademark) DISH 35 mm Type 903 (which had a spheroid well diameter of 800 μm, a spheroid well depth of 300 μm, and several spheroid wells to about 1,000 wells, and was manufactured by AGC Techno Glass Co., Ltd.) which was a cell non-adhesive 35 mm dish having recessed portions on the bottom surface, in a state in which hADSCs ($1.2 \times 10^6$ cells) and biocompatible polymer blocks (1 mg) were suspended in 4 mL of a medium.

[Example 14] Manufacturing and Evaluation of 2.5 Mass % Dextran Sodium Sulfate (DSS)-Induced Mouse Colitis Model As mice, SPF C57BL/6n female mice (Charles River Laboratories Japan, Inc.) which were 6 to 7 weeks old and weighed 17 to 21 g were used. The C57BL/6n female mice which were 6 weeks old were allowed to freely drink a 2.5 mass % DSS (MP Biomedicals, LLC.: Dextran Sodium Sulfate, molecular weight (MW)=36,000 to 50,000) aqueous solution, and the free drinking start date was set as the induction start date (Day 0). The mice were allowed to freely drink a 2.5 mass % DSS aqueous solution for seven days from the induction start date, the 2.5 mass % DSS aqueous solution were substituted with distilled water on the seventh day, and the mice were allowed to freely drink the distilled water for further seven days. Body weights of the respective mice were measured after 0, 1, 2, 5, 6, 7, 8, 9, 12, 13 and 14 days after the induction start date.

The evaluation of the colitis was performed with respect to a body weight and a length of a large intestine on the last day (14th day from the induction start). As the inflammation progressed, the body weight decreased, and in a case where the inflammation was recovered, the body weight increased. The length of the large intestine is used as a morphological parameter of degree of inflammation, and the inflammation causes the shortening of the large intestine (JIN SEOK PARK et al., J. CLIN. BIOCHEM. NUTR, 2015; 57: 192-203).

For the evaluation of the body weight, the body weight ratio (%) of each mouse to a normal mouse was calculated and evaluated. The body weight ratio (%) to a normal mouse was calculated according to the following (Equation 5) and (Equation 6). The body weight recovery rate (%) was obtained according to (Equation 7).

$$\text{The body weight ratio (\%) of each mouse with respect to that of Day } 0 = (Wt/W0) \times 100 \quad \text{(Formula 5)}$$

(In the formula, W0 indicates a body weight measurement value of the induction start date, and Wt indicates a body weight measurement value after t days from the induction start date. Here, t is 1, 2, 5, 6, 7, 8, 9, 12, 13, or 14, and W0 and Wt are the body weight of the same individual.)

$$\text{The body weight ratio (\%) of each mouse to normal mouse} = (Wt/W0) \times 100 \times (100/At) \quad \text{(Formula 6)}$$

(In the formula, W0 is a body weight measurement value of the induction start date, and Wt is a body weight measurement value after t days from the induction start date. With respect to each mouse to a normal mouse after t days from the induction start date, At is obtained by calculating the body weight ratios (%) with respect to that of Day 0 by (Formula 5) and averaging the body weight ratios. Here, t is 1, 2, 5, 6, 7, 8, 9, 12, 13, or 14, and W0 and Wt are the body weight of the same individual.)

$$\text{Body weight recovery rate (\%)} = ((Vt-Dt)-(Vt-Xt))/(Vt-Dt) \quad \text{(Equation 7)}$$

(In the formula, Vt represents an average value of a "body weight ratio to a normal mouse" of a normal mouse after t days from the induction start date. Dt indicates an average value of "a body weight ratio to a normal mouse" of an ADSC medium mouse group after day t from the induction start date. Xt indicates an average value of "a body weight ratio to normal mouse" of each mouse group after t days from the induction start date. Here, t is 1, 2, 5, 6, 7, 8, 9, 12, 13, or 14. The body weight recovery rate of the normal mouse group is 100% and the body weight recovery rate of ADSC medium mouse group is 0%.)

For the length of the large intestine, a length from an anal tip of each mouse to a cecum was measured so as to obtain a short intestine recovery rate was determined according to (Expression 8). (The recovery rate of the short intestine of the normal mouse group is 100%, the short intestine recovery rate of ADSC medium group is 0%.)

Short intestine recovery rate (%)=(($Lx-L2$)×100)/ ($L1-L2$)     (Formula 8)

(In the formula, L1 indicates a median value of lengths of large intestines of a normal mouse group, L2 indicates a median value of lengths of large intestines of an ADSC medium mouse group, and Lx indicates a median value of lengths of large intestines of each mouse group.)

[Example 15] Administration of Mosaic Cell Mass of hADSC to 2.5 Mass % DSS Colitis Model Mouse With respect to the 2.5 mass % DSS colitis model mouse manufactured in Example 14, the ADSC mosaic cell mass manufactured in Example 13 was intraperitoneally administered after one day from the induction start date. 1,000 hADSC mosaic cell masses ($1.2\times10^6$ cells of hADSC+1 mg/mouse of biocompatible polymer blocks) or 5,000 hADSC mosaic cell masses ($6.0\times10^6$ cells of hADSC+5 mg/mouse of biocompatible polymer blocks) were administered.

[Comparative Example 4] Administration of hADSC Cell Suspension or ADSC Medium to 2.5 Mass % DSS Colitis Model Mouse With respect to the 2.5 mass % DSS colitis model mouse manufactured in Example 14, a hADSC cell suspension in a state in which the cells which were the same as Example 13 were suspended in 200 μL of an ADSC medium after one day from the induction start date or 200 μL of the ADSC medium was intraperitoneally administered. The number of cells included in the hADSC cell suspension was set as $1.2\times10^6$ cells/mouse.

Average values of the body weight ratios (%) with respect to a normal mouse of each mouse group in Example 15 and Comparative Example 4 are presented in FIG. 6. As illustrated in FIG. 6, a "body weight ratio to a normal mouse" of the mouse group of 1,000 hADSC mosaic cell masses was higher than that of the ADSC medium mouse group which was the comparative example after 12, 13, and 14 days from the induction start date. The recovery of the body weight of the mouse group of 1,000 hADSC mosaic cell masses was faster than that of the ADSC medium mouse group. A "body weight ratio to a normal mouse" of the mouse group of 5,000 hADSC mosaic cell masses was higher than the ADSC medium mouse group which was the comparative example after 2, 5, 6, 7, 8, 9, 12, 13, and 14 days from the induction start date. In the mouse group of 5,000 hADSC mosaic cell masses, the decrease of the body weight was suppressed compared with the ADSC medium mouse group, and the recovery of the body weight was faster than that of the ADSC medium mouse group. On the last day (after 14th day from the induction start date), the body weight recovery rate in the mouse group of 1,000 hADSC mosaic cell masses was 39%, and the body weight recovery rate in the mouse group of 5,000 hADSC mosaic cell masses was 96%. In 1,000 hADSC mosaic cell masses and 5,000 hADSC mosaic cell masses, the effect of improvement of the decrease of the body weight was able to be exhibited. The improvement effect was higher in a case where the number of mosaic cell masses was greater.

Figure 7:
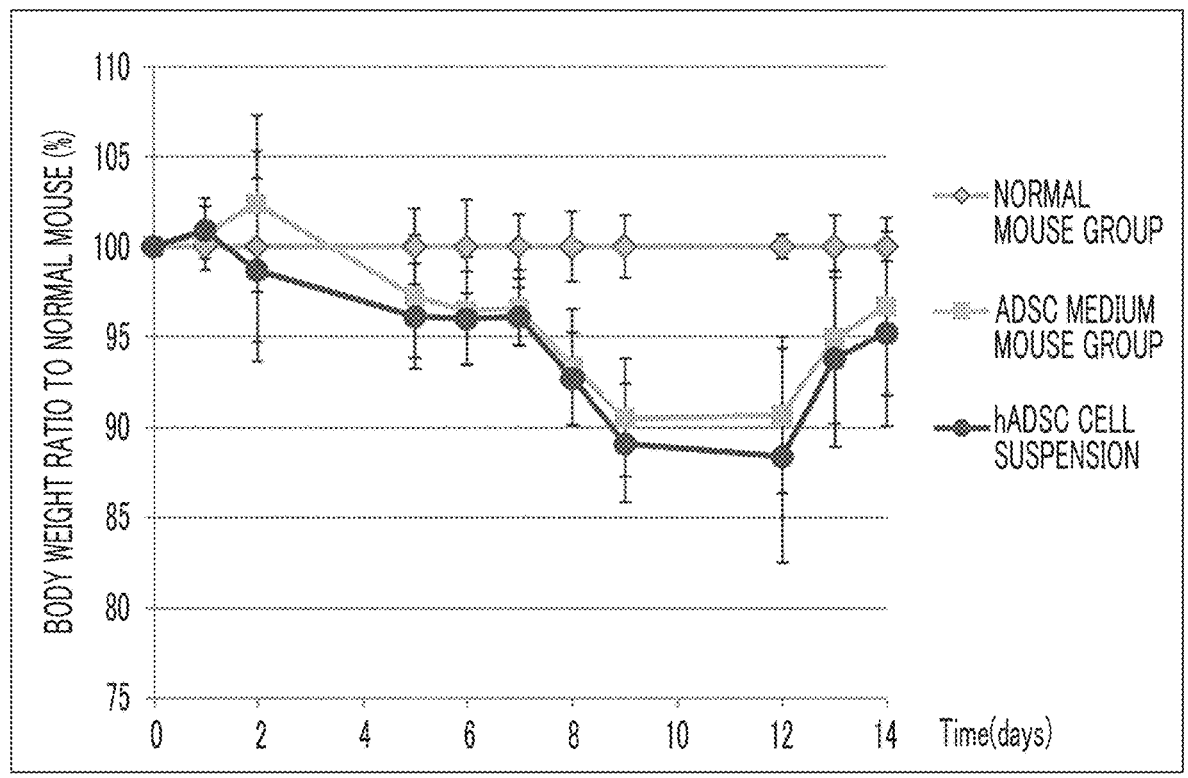
FIG. 7 illustrates results obtained by measuring body weights of 2.5 mass % dextran sodium sulfate (DSS)-induced mice.

In Comparative Example 4, an average value of the body weight ratio (%) of the normal mouse of each mouse group was provided in FIG. 7. As illustrated in FIG. 7, the hADSC cell suspension mouse group exhibited the same transition of the body weight of the ADSC medium mouse group after 2, 5, 6, 7, 8, and 9 days after the induction start date. After 12, 13 and 14 days of the induction start date, the "body weight ratio with respect to the normal mouse" than the ADSC medium mouse group. On the last day (after 14 days from the induction start date), the body weight recovery rate in the hADSC cell suspension mouse group was −44%. As described above, it is presented that the hADSC cell suspension did not improve the body weight decrease of the 2.5 mass % DSS colitis model mouse.

Collectively presenting the evaluation results of the body weight above, in the mouse group of 1,000 hADSC mosaic cell masses and the mouse group of 5,000 hADSC mosaic cell masses, the effect of improving the body weight decrease of the 2.5 mass % DSS colitis model mouse was recognized. Meanwhile, in the hADSC cell suspension mouse group having the same number of cells as the mouse group of 1,000 hADSC mosaic cell masses, a method of improving the body weight decrease of the 2.5 mass % DSS colitis model mouse was not recognized.

In Example 15, in the mouse group of 1,000 hADSC mosaic cell masses, the short intestine recovery rate was 75%, and in the mouse group of 5,000 hADSC mosaic cell masses, the short intestine recovery rate was 50%. It was recognized that 1,000 hADSC mosaic cell masses and 5,000 hADSC mosaic cell masses improve short intestinal transformation of the large intestine of the 2.5 mass % DSS colitis model mouse.

In Comparative Example 4, in the hADSC cell suspension mouse group, the short intestine recovery rate was 14%. It was recognized that the hADSC cell suspension improved the short intestinal transformation of the large intestine of the 2.5 mass % DSS colitis model mouse, but it was presented that the improvement effect of the short intestinal transformation of the large intestine was smaller than that of the 1,000 hADSC mosaic cell masses in which the same number of cells were administered.

Collectively presenting the evaluation results of the length of the large intestine, the effect that 1,000 hADSC mosaic cell masses and 5,000 hADSC mosaic cell masses improved the short intestinal transformation of the 2.5 mass % DSS colitis model mouse was recognized, and it was presented that the effect was greater than the effect of improving the short intestinal transformation of the hADSC cell suspension.

The result of the body weight and the length of the large intestine exhibits the inflammation improvement effect on the 2.5 mass % DSS colitis model mouse by the hADSC mosaic cell mass, and it was presented that the effect was greater than that of the hADSC cell suspension.

[Example 16] Manufacturing and Evaluation of 3.0 Mass % Dextran Sodium Sulfate (DSS)-Induced Mouse Colitis Model As the mice, SPF C57BL/6n female mice (Charles River Laboratories Japan, Inc.) which were six to seven weeks old and weighed 17 to 21 g were used.

Six week old C57BL/6n female mice were allowed to freely drink a 3.0 mass % DSS (MP Biomedicals LLC.: Dextran Sodium Sulfate, MW=36,000 to 50,000) aqueous solution. The free drinking start date was set as the induction start date (Day 0). The mice were allowed to freely drink the 3.0 mass % DSS aqueous solution for seven days from the induction start date, the 3.0 mass % DSS aqueous solution was substituted with the distilled water for seven days, and the mice were allowed to freely drink the distilled water for six days. Body weights of respective mice measured after 0, 1, 2, 5, 6, 7, 8, 9, 12, and 13 days from the induction start date. The colitis evaluation was performed by the body weight and the length of the large intestine on the last day (13th day from the induction start), in the same manner as Example 14.

[Example 17] Administering of hADSC Mosaic Cell Mass to 3.0 Mass % DSS Colitis Model Mouse The hADSC mosaic cell mass manufactured in Example 13 was intraperitoneally administered to the 3.0 mass % DSS colitis model mice manufactured in Example 16 after one day from the induction start date. 1,000 hADSC mosaic cell masses ($1.2 \times 10^6$ cells of hADSC+1 mg/mouse of biocompatible polymer blocks), or 5,000 hADSC mosaic cell masses ($6.0 \times 10^6$ cells of hADSC+5 mg/mouse of biocompatible polymer blocks) were administered.

[Comparative Example 5] Administering ADSC Medium to 3.0 Mass % DSS Colitis Model Mouse 200 μL of an ADSC medium was intraperitoneally administered to the 3.0 mass % DSS colitis model mouse manufactured in Example 16 after one day from the induction start date.

Figure 8:
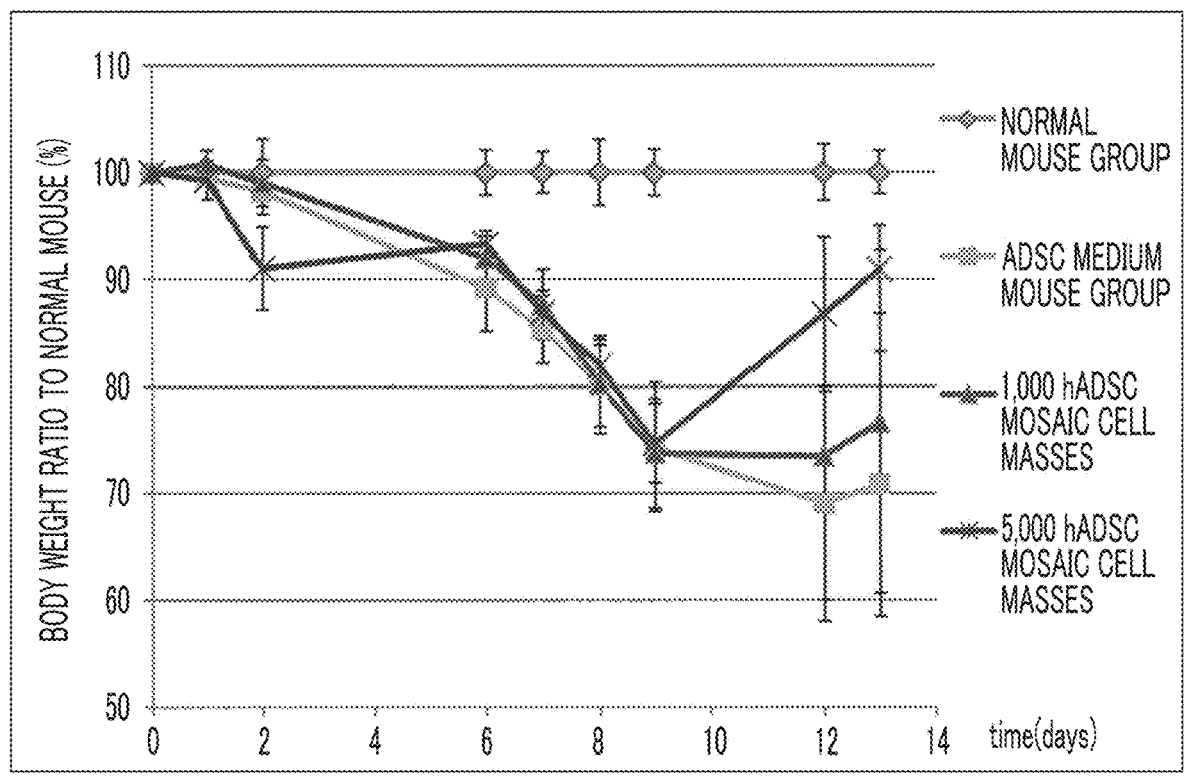
FIG. 8 illustrates results obtained by measuring body weights of 3.0 mass % dextran sodium sulfate (DSS)-induced mice.

In Example 17 and Comparative Example 5, the average value of the body weight ratios (%) of the normal mice in the respective mouse groups is presented in FIG. 8. As illustrated in FIG. 8, the mouse group of 1,000 hADSC mosaic cell masses had a higher "body weight ratio to a normal mouse" than the ADSC medium mouse group which was the comparative example after 12 and 13 days from the induction start date. It was presented that, the recovery of the body weight of the mouse group of 1,000 hADSC mosaic cell masses was faster than that of the ADSC medium mouse group. After 12 and 13 days from the induction start date, a "body weight ratio to a normal mouse" of the mouse group of 5,000 hADSC mosaic cell masses was greater than that of the ADSC medium mouse group which was the comparative example and further the body weight ratio thereof was greater than that of the mouse group of the 1,000 hADSC mosaic cell masses. On the last day (after 13 days from the induction start date), the body weight recovery rate of the mouse group of 1,000 hADSC mosaic cell masses was 20%, and the body weight recovery rate of the mouse group of 5,000 hADSC mosaic cell masses was 69%. In 1,000 hADSC mosaic cell masses and 5,000 ADSC mosaic cell masses, the improvement effect of the body weight decrease was recognized. The improvement effect thereof was greater in a case where the number of the mosaic cell mass was greater.

In Example 17 and Comparative Example 5, in the mouse group of 1,000 hADSC mosaic cell masses, the short intestine recovery rate was 68%, and in the mouse group of 5,000 hADSC mosaic cell masses, the short intestine recovery rate was 81%. It was recognized that 1,000 hADSC mosaic cell masses and 5,000 hADSC mosaic cell masses improved the short intestinal transformation of the large intestine of the 3.0 mass % DSS colitis model mouse.

From the results of the body weight and the length of the large intestine, the inflammation improvement effect on the 3.0 mass % DSS colitis model mouse by the hADSC mosaic cell mass was recognized.

[Example 18] Manufacturing and Evaluation of 3.0 Mass % Dextran Sodium Sulfate (DSS)-Induced Mouse Colitis Model As the mice, SPF C57BL/6n female mice (Charles River Laboratories Japan, Inc.) which were six to seven weeks old and weighed 17 to 21 g were used.

Six week old C57BL/6n female mice were allowed to freely drink a 3.0 mass % DSS (MP Biomedicals LLC.: Dextran Sodium Sulfate, MW=36,000 to 50,000) aqueous solution. The free drinking start date was set as the induction start date (Day 0). The mice were allowed to freely drink the 3.0 mass % DSS aqueous solution for seven days from the induction start date, the 3.0 mass % DSS aqueous solution was substituted with distilled water on the seventh day, and the mice were allowed to freely drink the distilled water for further seven days. The body weights of the respective mice were measured after 0, 1, 4, 5, 6, 7, 8, 11, 12, 13, and 14 days from the induction start date. The colitis evaluation was performed by the weight, the length of the large intestine on the last day (14th day from the induction start), and the pathological evaluation of the large intestine on the last day.

The evaluation of the body weight and the length of the large intestine was performed in the same manner as Example 14.

In the pathological evaluation, a tissue of the large intestine removed on the final day was fixed with formalin, and embedded in paraffin, sliced, and stained with hematoxylin and eosin (HE staining).

The manufactured specimens were evaluated for ulcer depth, ulcer breadth, edema, and inflammatory cell infiltration with an optical microscope. The evaluation of the depth of the ulcer is as follows: 0 points: the epithelium was complete, 1 point: there was injury to a mucosal lamina propria, 2 points: there was injury reaching a submucosal layer, and 3 points: there was injury reaching a serosa. The evaluation of the extent of the ulcer is as follows: 0 points: an area ratio with injury was 0%, 1 point: an injury area ratio was greater than 0% and 25% or less, 2 points: an injury area ratio was greater than 25% and 50% or less, 3 points: an injury area ratio was greater than 50% and 75% or less, and 4 points: an injury area ratio was greater than 75%. Evaluation of edema and inflammatory cell infiltration is as follows: 0 points: edema and inflammatory cell infiltration were not observed, 1 point: mild, 2 points: moderate, 3 points: advanced, and 4 points: further advanced. By the method above, three points of the upper part of the colon, the lower part of the colon, and the rectum of each mouse were evaluated, and the total score of the above three parts was comprehensively evaluated as the pathology score. The pathology score is higher as the inflammation occurs.

[Example 19] Administering of hADSC Mosaic Cell Mass to 3.0 Mass % DSS Colitis Model Mouse 1,000 hADSC mosaic cell masses ($1.2 \times 10^6$ cells of hADSC+1 mg/mouse of biocompatible polymer block) manufactured in Example 13 to the 3.0 mass % DSS colitis model mouse manufactured in Example 18 after seven days from the induction start date and intraperitoneally administered in a state of being suspended in 400 μL of the ADSC medium.

[Comparative Example 6] Administering of hADSC Cell Suspension or ADSC Medium to 3.0 Mass % DSS Colitis Model Mouse A hADSC cell suspension in a state in which the cells as in Example 13 were suspended in 400 μL of ADSC medium or 400 μL of ADSC medium was intraperitoneally administered to the 3.0 mass % DSS colitis model mouse manufactured in Example 18. The number of cells included in the hADSC cell suspension was set as $1.2 \times 10^6$ cells/mouse.

Figure 9:
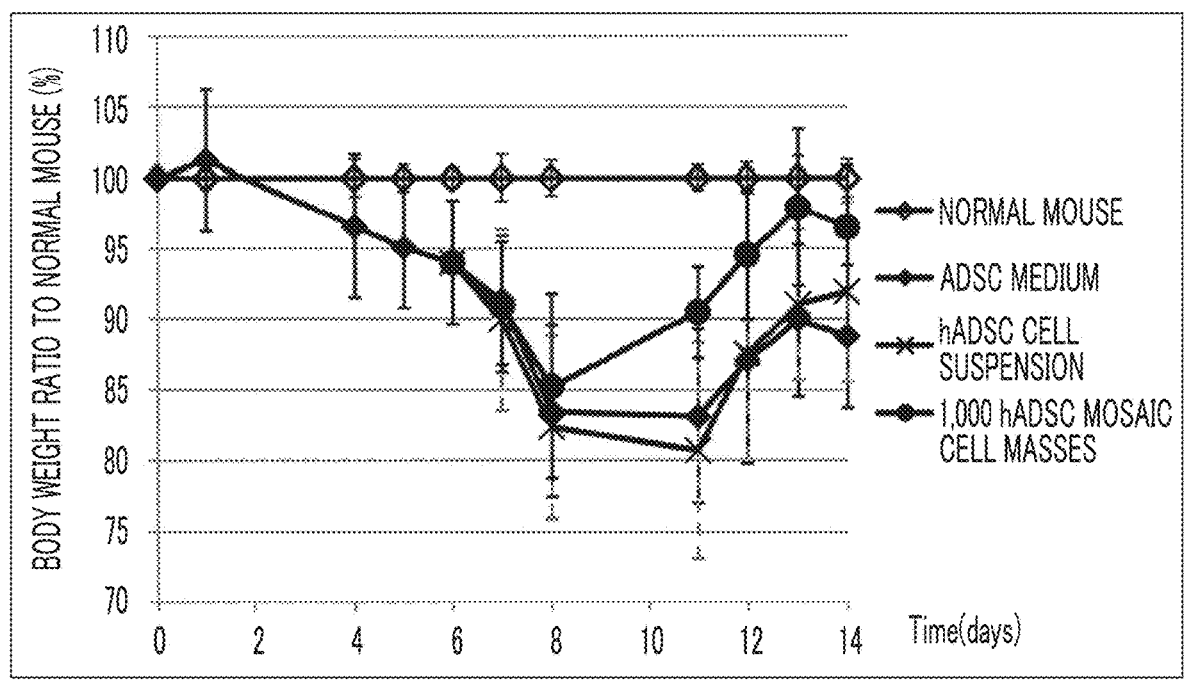
FIG. 9 illustrates results obtained by measuring body weights of 3.0 mass % dextran sodium sulfate (DSS)-induced mice.

In Example 19 and Comparative Example 6, the average values of the body weight ratios (%) of respective mouse groups to the normal mice are presented in FIG. 9. As illustrated in FIG. 9, the "body weight ratio to the normal mouse" of the mouse group of 1,000 hADSC mosaic cell masses was higher than those of the ADSC medium mouse group and the hADSC cell suspension mouse group which were comparative examples after 11, 12, 13, and 14 days from the induction start date. The recovery of the body weight of the mouse group of 1,000 hADSC mosaic cell masses was faster than those of the ADSC medium mouse group and the hADSC cell suspension mouse group. Accordingly, with respect to the 1,000 hADSC mosaic cell masses, the improvement effect of the body weight decrease was recognized.

Meanwhile, as presented in FIG. 9, the hADSC cell suspension mouse group exhibited the transition of the body weight which was the same as the ADSC medium mouse group after 11, 12, 13 and 14 days from the induction start date. Accordingly, the improvement effect of the body weight decrease of the hADSC cell suspension was not recognized.

Collectively presenting the evaluation results of the body weight, an effect that the 1,000 hADSC mosaic cell masses improved the body weight decrease of the 3.0 mass % DSS colitis model mouse was recognized. Meanwhile, an effect that the hADSC cell suspension improved the body weight decrease of the 3.0 mass % DSS colitis model mouse was not recognized.

Figure 10:
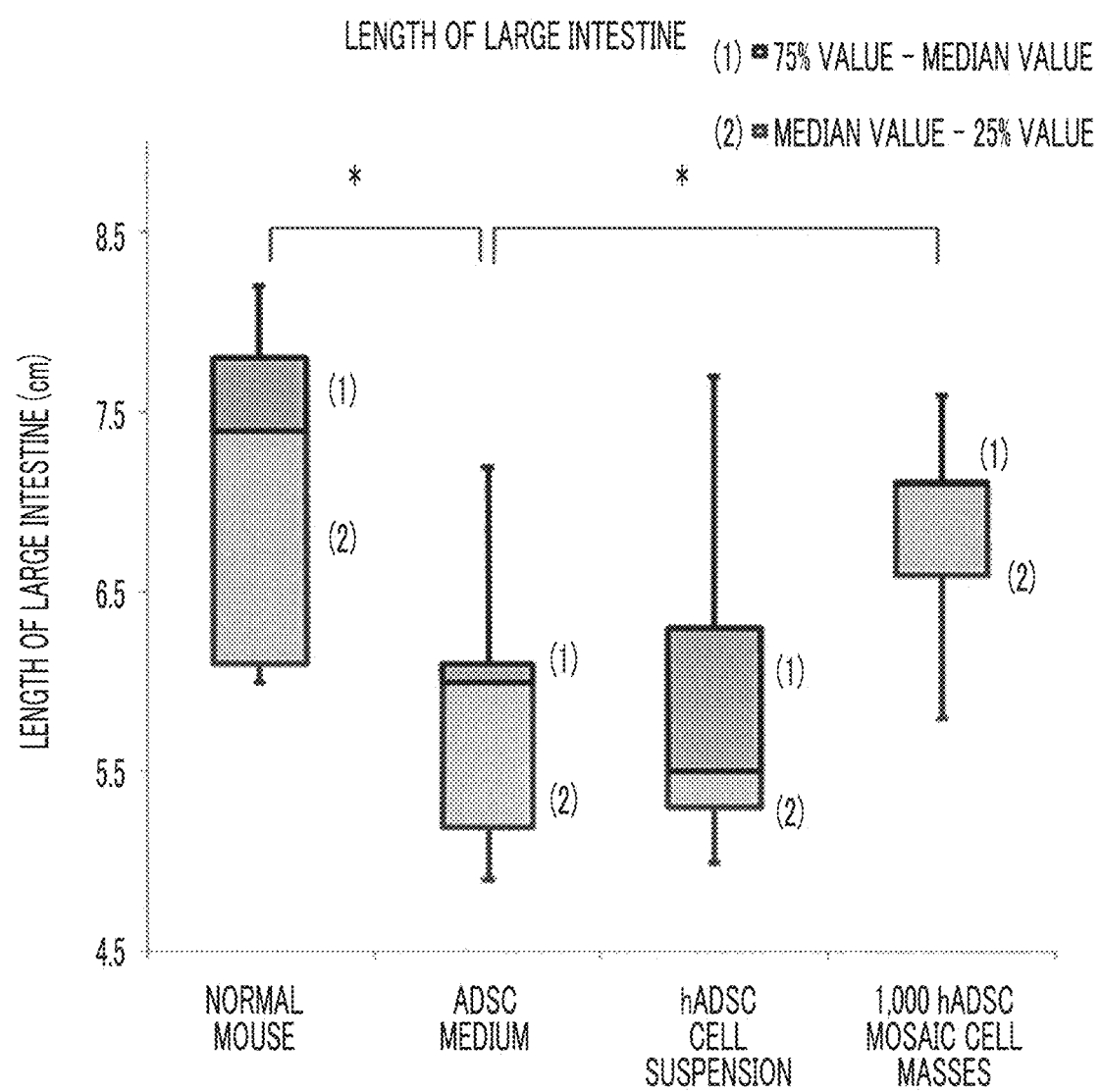
FIG. 10 illustrates results obtained by measuring lengths of large intestines of 3.0 mass % dextran sodium sulfate (DSS)-induced mice.

In Example 19 and Comparative Example 6, the lengths of the large intestines of the respective mouse groups are presented in FIG. 10, as a box plot diagram (*: P<0.05 (t test in the figure)).

As presented in FIG. 10, the length of the large intestine of the ADSC medium mouse group was significantly shorter than that of the normal mouse group.

In Example 19, the length of the large intestine of the mouse group of 1,000 hADSC mosaic cell masses was significantly longer than that of the ADSC medium mouse group which was the comparative example. Accordingly, it was recognized that 1,000 hADSC mosaic cell masses improved the short intestinal transformation of the large intestine of the 3.0 mass % DSS colitis model mouse.

Meanwhile, the length of the large intestine of the hADSC cell suspension mouse group in Comparative Example 6 was not different from that of the ADSC medium mouse group which was the comparative example. Accordingly, it was recognized that the hADSC cell suspension did not improve the short intestinal transformation of the large intestine of the 3.0 mass % DSS colitis model mouse.

As the median value of the lengths of the large intestines of the respective mouse groups, the normal mouse group had 7.4 cm, the ADSC medium mouse group had 6.0 cm, the hADSC cell suspension mouse group had 5.5 cm, and the mouse group of 1,000 hADSC mosaic cell masses had 7.1 cm.

Collectively presenting the evaluation results of the lengths of the large intestines, an effect that the 1,000 hADSC mosaic cell masses improved the short intestinal transformation of the 3.0 mass % DSS colitis model mouse was recognized. Meanwhile, an effect that the hADSC cell suspension improved the short intestinal transformation of the 3.0 mass % DSS colitis model mouse was not recognized.

Figure 11:
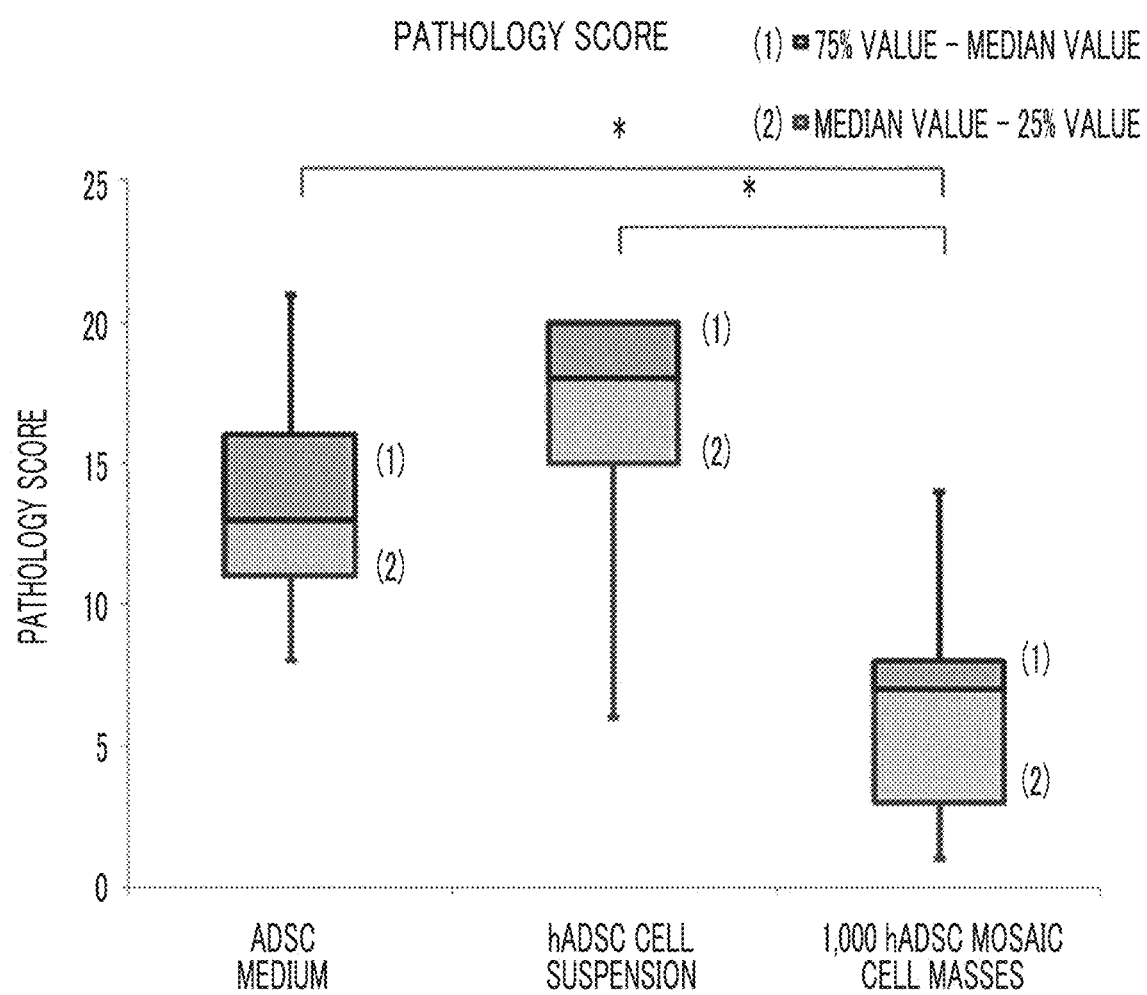
FIG. 11 illustrates pathology scores of 3.0 mass % dextran sodium sulfate (DSS)-induced mice.

In Example 19 and Comparative Example 6, the pathology scores of the respective mouse groups are presented in FIG. 11 as a box plot diagram (*: P<0.05 (t test)). As presented in FIG. 11, in Example 19, the pathology scores of the mouse groups of 1,000 hADSC mosaic cell masses were significantly lower than those of the ADSC medium mouse group and the hADSC cell suspension mouse group which were the comparative examples. Accordingly, it was recognized that 1,000 hADSC mosaic cell masses improved the inflammation of the large intestine of the 3.0 mass % DSS colitis model mouse.

Meanwhile, in Comparative Example 6, it was recognized that the pathology score of the hADSC cell suspension mouse group was not different from that of the ADSC medium mouse group which was the comparative example. Accordingly, it was recognized that the hADSC cell suspension did not improve the inflammation of the large intestine of the 3.0 mass % DSS colitis model mouse.

As the median values of the pathology scores of the respective mouse groups, the normal mouse group had 0 points, the ADSC medium mouse group had 13.0 points, the hADSC cell suspension mouse group had 18.0 points, the mouse group of 1,000 hADSC mosaic cell masses had 7.0 points.

The median values of the pathology scores of the respective parts (upper colon, lower colon, and rectum) of the respective mouse groups are presented in Table 2.

TABLE 2

| | Median value (point) of pathology scores of respective parts | | |
|---|---|---|---|
| | Upper colon | Lower colon | rectum |
| Normal mouse group | 0 | 0 | 0 |
| ADSC medium mouse group | 3 | 8 | 3 |
| hADSC cell suspension mouse group | 2 | 8 | 8 |
| Mouse group of 1,000 hADSC mosaic cell masses | 1 | 6 | 0 |

Figure 12:
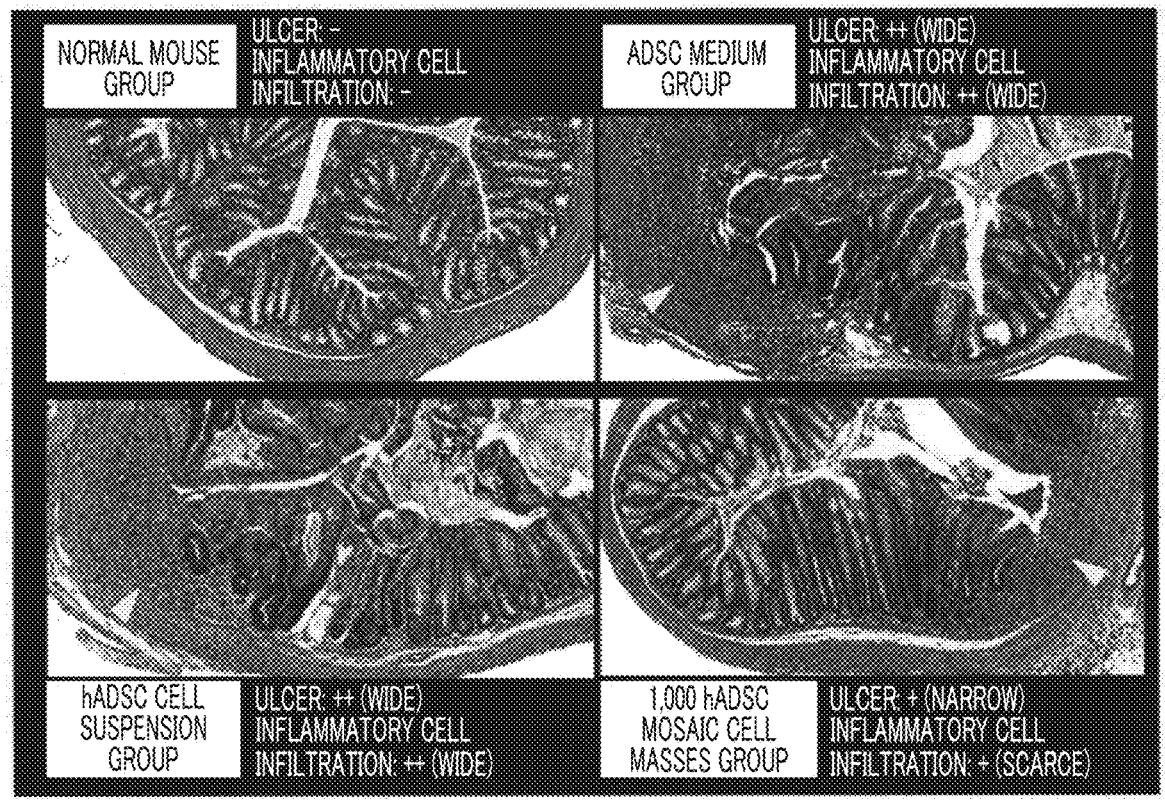
FIG. 12 illustrates representative HE tissue stained images of respective groups of mice.
Figure 13:
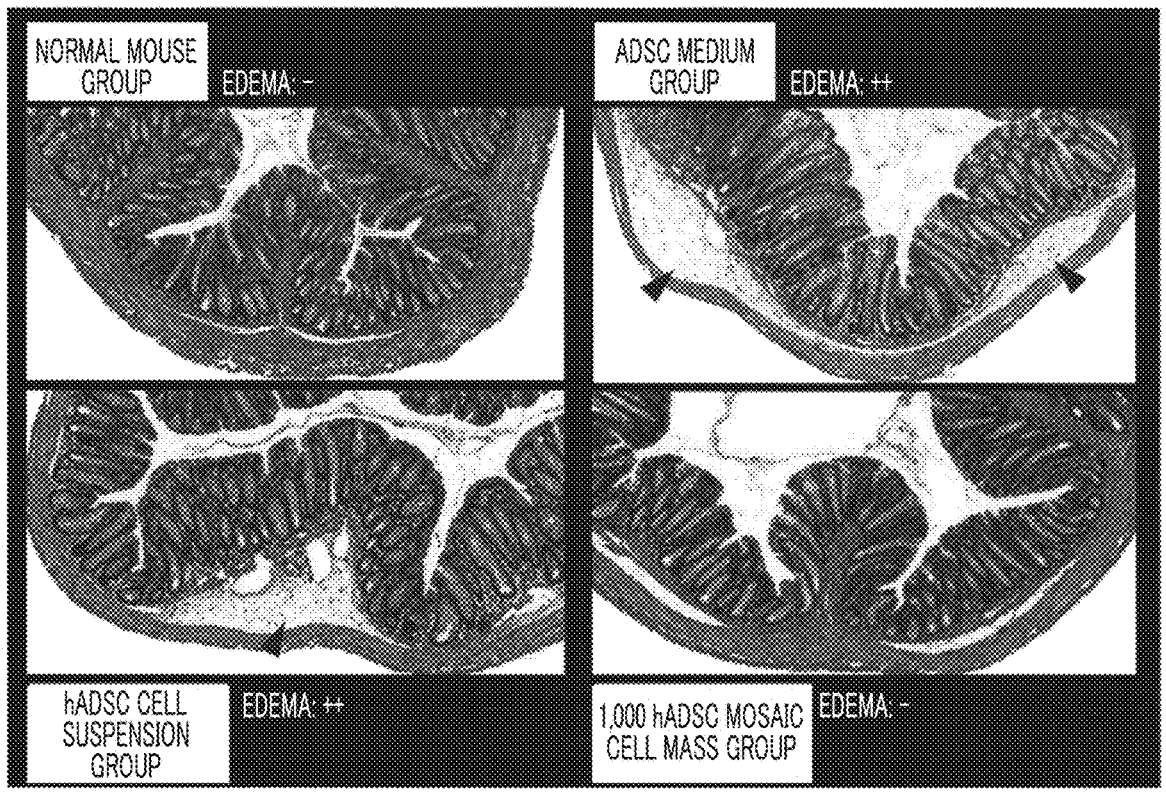
FIG. 13 illustrates representative HE tissue stained images of respective groups of mice.

In Example 19 and Comparative Example 6, representative HE tissue stained images of the respective mouse groups are illustrated in FIGS. 12 and 13. As illustrated in FIGS. 12 and 13, ulcer, inflammatory cell infiltration, and edema were not recognized in the normal mouse group. Ulcer, inflammatory cell infiltration, and edema were widely recognized in the ADSC medium mouse group which was the comparative example. As in the ADSC medium mouse group, ulcer, inflammatory cell infiltration, and edema were widely recognized in the hADSC cell suspension mouse group.

Meanwhile, in Example 19, ranges of ulcer and inflammatory cell infiltration were small in the mouse group of 1,000 hADSC mosaic cell masses. Edema was not observed.

Collectively presenting the result of the pathological evaluation, it was recognized that 1,000 hADSC mosaic cell masses had an effect of treating inflammation of the 3.0 mass % DSS colitis model mouse. Meanwhile, it was not recognized that the hADSC cell suspension had an effect of treating inflammation of the 3.0 mass % DSS colitis model mouse.

From the results of the body weight, the length of the large intestine and the pathological evaluation, the inflammation improvement effect on the 3.0 mass % DSS colitis model mouse by the hADSC mosaic cell mass was recognized.

[Example 20] Manufacturing of hBMSC Mosaic Cell Mass

Human bone marrow derived mesenchymal stem cells (hBMSC: Human Bone Marrow Derived Mesenchymal Stem Cells) were suspended in a proliferation medium (Takara Bio Inc.: MSCGM Bullet Kit (trademark)), and biocompatible polymer blocks (53 to 106 µm) manufactured in Example 3 were added thereto. The mixture was sown in EZSPHERE (registered trademark) DISH 35 mm Type 903 (which had a spheroid well diameter of 800 µm, a spheroid well depth of 300 µm, and several spheroid wells to about 1,000 wells, and was manufactured by AGC TECHNO GLASS CO., Ltd.) which was a cell non-adhesive 35 mm dish having recessed portions on the bottom surface thereof, in a state in which hBMSCs ($2.0 \times 10^5$ cells) and biocompatible polymer blocks (0.2 mg) were finally suspended in 4 mL of a medium.

After standing at 37° C. for 20 hours in a $CO_2$ incubator, it was able to collect a plurality of mosaic cell masses as a spherical shape formed of the hBMSC and the biocompatible polymer block having a diameter of about 0.2 mm.

[Comparative Example 7] Manufacturing of hBMSC Cell Mass

Human bone marrow derived mesenchymal stem cells (hBMSCs) were suspended in a proliferation medium (Takara Bio Inc.: MSCGM Bullet Kit (trademark)). The mixture was sown in EZSPHERE (registered trademark) DISH 35 mm Type 903 (which had a spheroid well diameter of 800 µm, a spheroid well depth of 300 µm, and several spheroid wells to about 1,000 wells, and was manufactured by AGC TECHNO GLASS CO., Ltd.) which was a cell non-adhesive 35 mm dish having recessed portions on the bottom surface thereof, in a state in which hBMSCs ($2.0 \times 10^5$ cells) were finally suspended in 4 mL of a medium.

After standing at 37° C. for 20 hours in a $CO_2$ incubator, it was able to collect a plurality of cell masses formed of the hBMSC only.

[Example 21] Proliferation Suppression Test of T Cell (hBMSC Mosaic Cell Mass)

The proliferation suppression ability of the T cells of the hBMSC mosaic cell masses manufactured in Example 20 was evaluated. T cells ($1.0 \times 10^5$ cells/well) flagged with the hBMSC mosaic cell mass ($5.0 \times 10^4$ cells of hBMSC+0.2 mg/well of biocompatible polymer block) and CFSE (cat #: 565082 (BD Biosciences)) were co-cultured for five days in 24 well plates. Cultivation was performed in a culture medium (hereinafter, referred to as a T cell medium) obtained by supplementing anti-CD3CD28 antibody beads (Dynabeads (Trademark): Human T-Activator CD3/CD28 (cat #: DB11161 (VERITAS Corporation)) in a RPMI1640 medium containing 2 mM glutamine, 100 IU/mL penicillin, 100 ug/ml streptomycin, 10% FBS, and 50 uM monothioglycerol. As the anti-CD3CD28 antibody beads, 10 µl of anti-CD3CD28 antibody beads were used per $1.0 \times 10^5$ cells of the T cells according to the method of using a product.

After co-culturing for 5 days, an average number of divisions of T cells co-cultured with hBMSC mosaic cell mass was measured using the CFSE fluorescence strength as an index. The fluorescence signal of CFSE stained before co-culturing is attenuated with the cell division, and thus the number of cell divisions can be identified by measuring the CFSE fluorescence strength. The average number of divisions of T cells was calculated by Formula 9.

Average number of cell divisions of $T$ cells (times)= (((the number of $T$ cells divided zero times)× 0)+((the number of $T$ cells divided one time)× 1)+((the number of $T$ cells divided two times)× 2)+((the number of $T$ cells divided three times)×3)+((the number of $T$ cells divided four times)×4)+((the number of $T$ cells divided five times)×5)+((the number of $T$ cells divided six times)×6))/(total value of the number of $T$ cells divided 0, 1, 2, 3, 4, 5, and 6 times)   (Formula 9)

[Comparative Example 8] T Cell Proliferation Suppression Test (hBMSC Cell Mass)

In the same manner as Example 21, with respect to the hBMSC cell mass manufactured in Comparative Example 7, T cell proliferation suppression ability was evaluated.

The hBMSC cell masses ($5.0 \times 10^4$ cells/well of hBMSC) and T cells ($1.0 \times 10^5$ cells/well) flagged with CFSE were co-cultured on 24 well plates for five days. The culturing was performed in the same T cell medium as in Example 21.

After co-culturing for five days, the CFSE fluorescence strength of T cells co-cultured with the hBMSC cell mass was measured, so as to calculate the average number of cell divisions of the T cells according to Formula 9.

Figure 14:
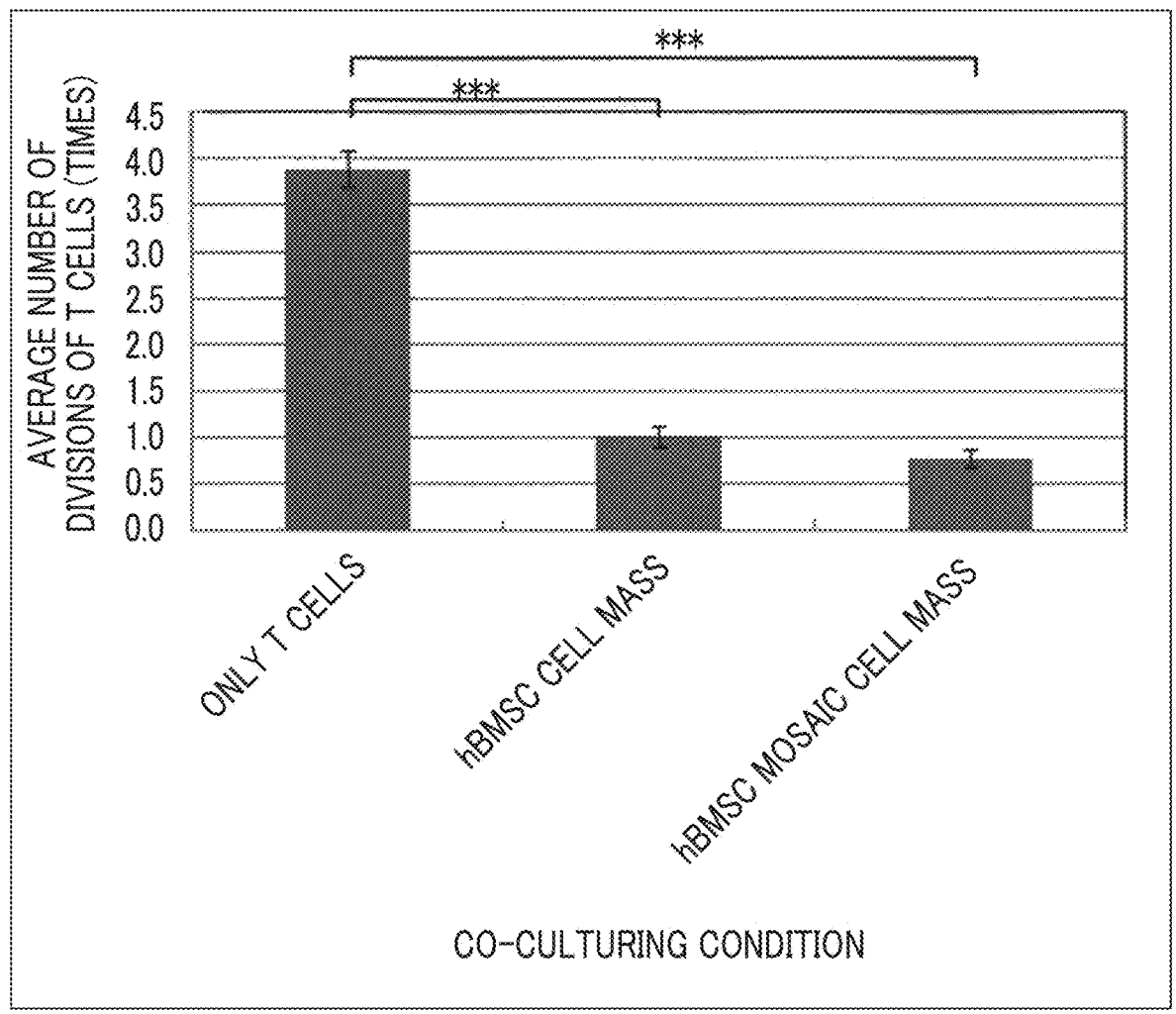
FIG. 14 illustrates results obtained by measuring mean division numbers of T cells.

The measuring results of the average number of cell divisions of the T cells are presented in FIG. 14 (in the figure, ***: P<0.001 (t test)). As a result, compared with a case where only T cells were cultured, the average number of cell divisions of the hBMSC mosaic cell mass and the T cells in a case of being co-cultured with the hBMSC cell mass was significantly decreased. Compared with a case of being co-cultured with the hBMSC cell mass, the average number of cell divisions of the T cells in a case of being co-cultured with the hBMSC mosaic cell mass was decreased. Accordingly, the hBMSC mosaic cell mass and the hBMSC cell mass exhibited T cell proliferation suppression ability, and the effect thereof was greater in the hBMSC mosaic cell mass.

The average number of cell divisions of the T cells in the respective culturing conditions was 3.87±2.60 times in a case where only the T cells were cultured, 1.00±0.12 times in a case of being co-cultured with the hBMSC cell mass, 0.77±0.10 times in a case of being co-cultured with the hBMSC mosaic cell mass.

[Example 22] Manufacturing of hADSC Mosaic Cell Mass

Human adipose derived stem cells (hADSC) were suspended in a proliferation medium (Lonza: ADSC-BulletKit (trademark), hereinafter also referred to as an ADSC medium), and biocompatible polymer blocks (53 to 106 µm) manufactured in Example 3 were added and was sown in EZSPHERE (registered trademark) DISH 35 mm Type 903

(which had a spheroid well diameter of 800 μm, a spheroid well depth of 300 μm, and several spheroid wells to about 1,000 wells, and was manufactured by AGC TECHNO GLASS CO., Ltd.) which was a cell non-adhesive 35 mm dish having recessed portions on the bottom surface thereof, in a state in which hADSCs ($2.0 \times 10^5$ cells) and biocompatible polymer blocks (0.2 mg) were finally suspended in 4 mL of a medium.

After standing at 37° C. for 20 hours in a $CO_2$ incubator, it was possible to collect a plurality of mosaic cell masses in a spherical shape having a diameter of about 0.2 mm which was formed of hADSC and biocompatible polymer blocks.

[Example 23] T Cell Activation Suppression Test
(IL-2 Release Amount Test)

The mosaic cell masses ($5.0 \times 10^4$ cells+0.2 mg/well of biocompatible polymer blocks) obtained in Examples 20 and 22 were respectively co-cultured with T cells and IL-2 released to the culture supernatant was quantified after 48 hours. In a case where the T cells are in an activation state, the T cells secrete IL-2, and thus the degree of T cell activation can be classified by quantifying IL-2. The culturing was performed in the same T cell medium as in Example 21. The number of T cells per well was set as $1.0 \times 10^5$ cells/well.

In the quantification, Human IL-2 ELISA Kit (cat #: RAB0286 (SIGMA-ALDRICH Corporation)) was used.

[Comparative Example 9] T Cell Activation Suppression Test (IL-2 Release Amount Test)

The same cells ($5.0 \times 10^4$ cells/well) as in Examples 20 and 22 cultured in an adhered state were respectively co-cultured with the T cells, and IL-2 released to the culture supernatant was quantified after 48 hours. The culturing was performed in the same T cell medium as in Example 21. The number of T cells per well was set as $1.0 \times 10^5$ cells/well.

In the quantification, Human IL-2 ELISA Kit (cat #: RAB0286 (SIGMA-ALDRICH Corporation)) was used.

Figure 15:
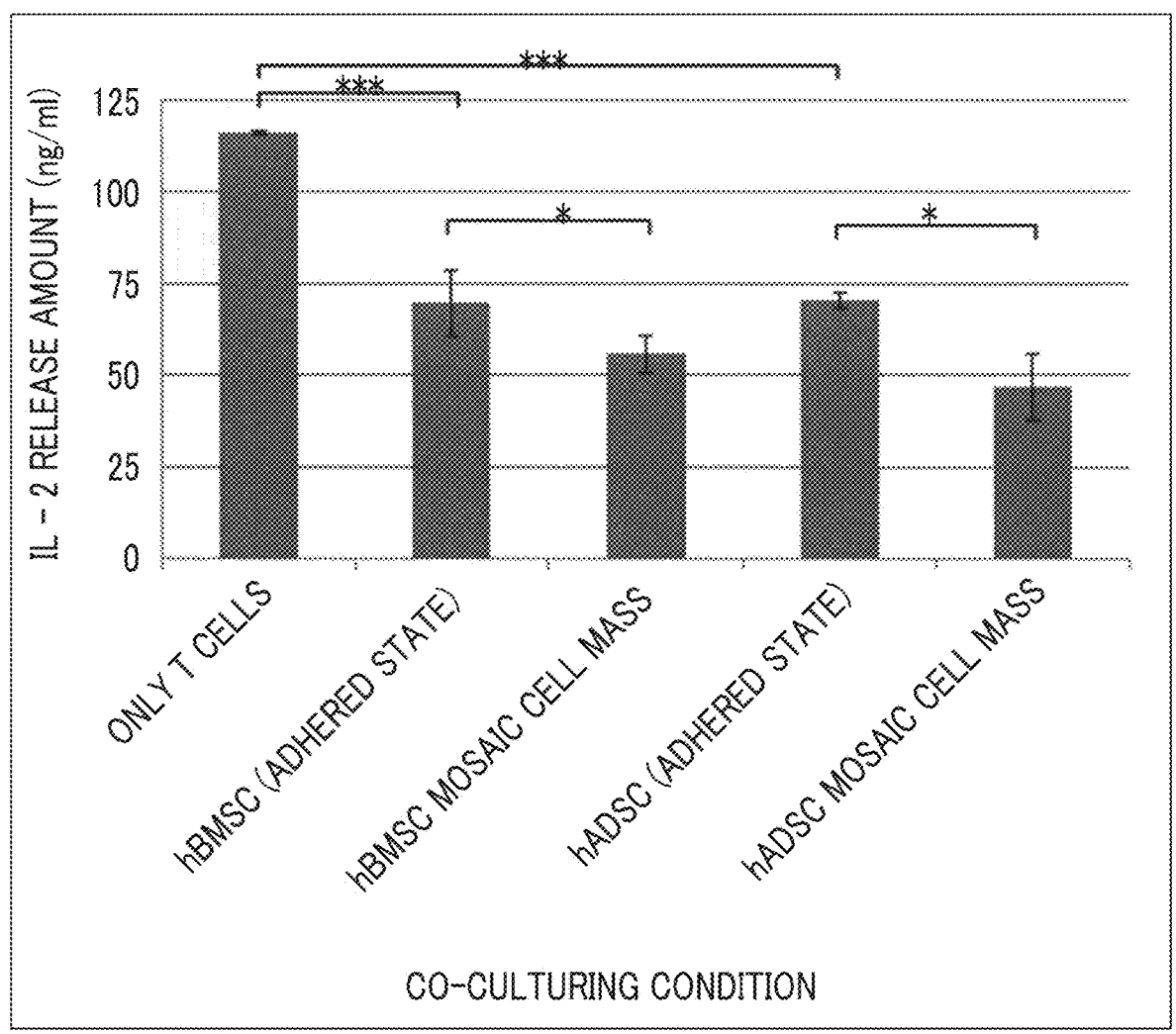
FIG. 15 illustrates quantitative results of IL-2.

The quantitative results of IL-2 measured in Example 23 and Comparative Example 9 are presented in FIG. 15 (in the figure, *: $P<0.05$, ***: $P<0.001$ (t test)). As a result, in a case of being co-cultured with the hBMSC mosaic cell mass and the hBMSC (adhesion state), the IL-2 release amount of the T cells was significantly decreased compared with a case where only the T cells were cultured. Compared with a case of being co-cultured with hBMSC (adhesion state), the IL-2 release amount of the T cells co-cultured with the hBMSC mosaic cell mass was significantly decreased. Accordingly, the hBMSC mosaic cell mass and the hBMSC (adhesion state) exhibited T cell activation suppression ability, and the effect thereof was greater in the hBMSC mosaic cell mass.

In the same manner, the IL-2 release amount in a case of being co-cultured with the hADSC mosaic cell mass and hADSC (adhesion state) was significantly decreased compared with a case where only the T cells were cultured. Compared with a case of being co-cultured with hADSC (adhesion state), the IL-2 secretion amount of the T cells co-cultured with the hADSC mosaic cell mass was significantly decreased. Accordingly, the hADSC mosaic cell mass and hADSC (adhesion state) exhibited the activation suppression ability of the T cells, and the effect thereof was greater in the hADSC mosaic cell mass.

[Example 24] Manufacturing of Dog Derived Cell Mosaic Cell Mass

Canine adipose derived stem cells (cADSC: Canine Adipose derived Stem Cells) were suspended in a DMEM medium (hereinafter, referred to as a cADSC medium) containing 10% FBS and 1% penicillin streptomycin, biocompatible polymer blocks (53 to 106 μm) manufactured in Example 3 were added and were sown in EZSPHERE (registered trademark) DISH 35 mm Type 903 (which had a spheroid well diameter of 800 μm, a spheroid well depth of 300 μm, and several spheroid wells to about 1,000 wells, and was manufactured by AGC TECHNO GLASS CO., Ltd.) which was a cell non-adhesive 35 mm dish having recessed portions on the bottom surface thereof, in a state in which cADSC ($1.2 \times 10^6$ cells) and biocompatible polymer blocks (0.25 mg) were finally suspended in 4 mL of a medium.

After standing at 37° C. for 69 hours in a $CO_2$ incubator, it was possible to collect a plurality of mosaic cell masses in a spherical shape having a diameter of about 0.2 mm which was formed of cADSC and biocompatible polymer blocks.

[Example 25] Effect of Treating Inflammation in Dog Derived Cell Mosaic Cell Mass In the same manner as in Example 19, with respect to the 3.0 mass % DSS colitis model mouse of Example 18, after seven days from the inflammation induction start date, cADSC mosaic cell masses ($1.2 \times 10^6$ cells of cADSC+0.25 mg/mouse biocompatible polymer blocks) manufactured in Example 24 were intraperitoneally administered in a state of being suspended in 400 μL of a cADSC medium.

[Comparative Example 10] Effect of Treating Inflammation in cADSC Cell Suspension or ADSC Medium In the same manner as in Example 25, with respect to the 3.0 mass % DSS colitis model mouse of Example 18, after seven days from the induction start date, the cADSC cell suspension in a state in which the cells as in Example 25 were suspended in 100 μL of a cADSC medium and 100 μL of a cADSC medium was administered by tail vein. The number of the cells included in the cADSC cell suspension was set as $4.0 \times 10^4$ cells/mouse or $1.2 \times 10^6$ cells/mouse.

Figure 16:
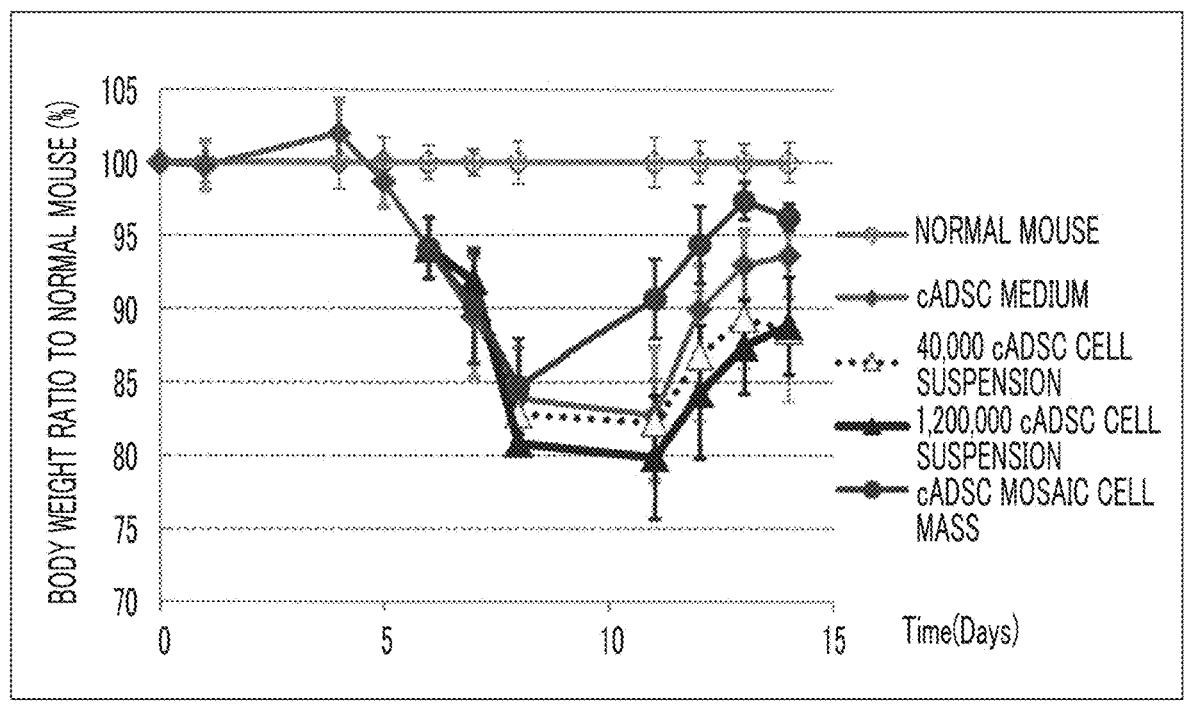
FIG. 16 illustrates average values of body weight ratios (%) of respective mouse groups to normal mice.

In Example 25 and Comparative Example 10, average values of body weight ratios (%) of the respective mouse groups to the normal mice are presented in FIG. 16. As illustrated in FIG. 16, the "body weight ratios to the normal mouse" of the cADSC mosaic cell mass mouse group after 11, 12, 13, and 14 days from the induction start date were greater than those of the cADSC medium mouse group and the cADSC cell suspension mouse group which were the comparative examples. The recovery of the body weight of the cADSC mosaic cell mass mouse group was faster than those of the ADSC medium mouse group and the cADSC cell suspension mouse group. Accordingly, it was recognized that the cADSC mosaic cell mass had an effect of improving the body weight decrease.

Meanwhile, as presented in FIG. 16, after 11, 12, 13, and 14 days from the induction start date, the cADSC cell suspension mouse group exhibited the transition of the body weight which was lower than that of the cADSC medium mouse group. Accordingly, it was not recognized that the cADSC cell suspension had an effect of improving the body weight decrease.

Collectively presenting results of evaluating the body weights, it was recognized that the cADSC mosaic cell mass had an effect of improving the body weight decrease of the 3.0 mass % DSS colitis model mouse. Meanwhile, it was not recognized that the cADSC cell suspension had an effect of improving the body weight decrease of the 3.0 mass % DSS colitis model mouse.

Figure 17:
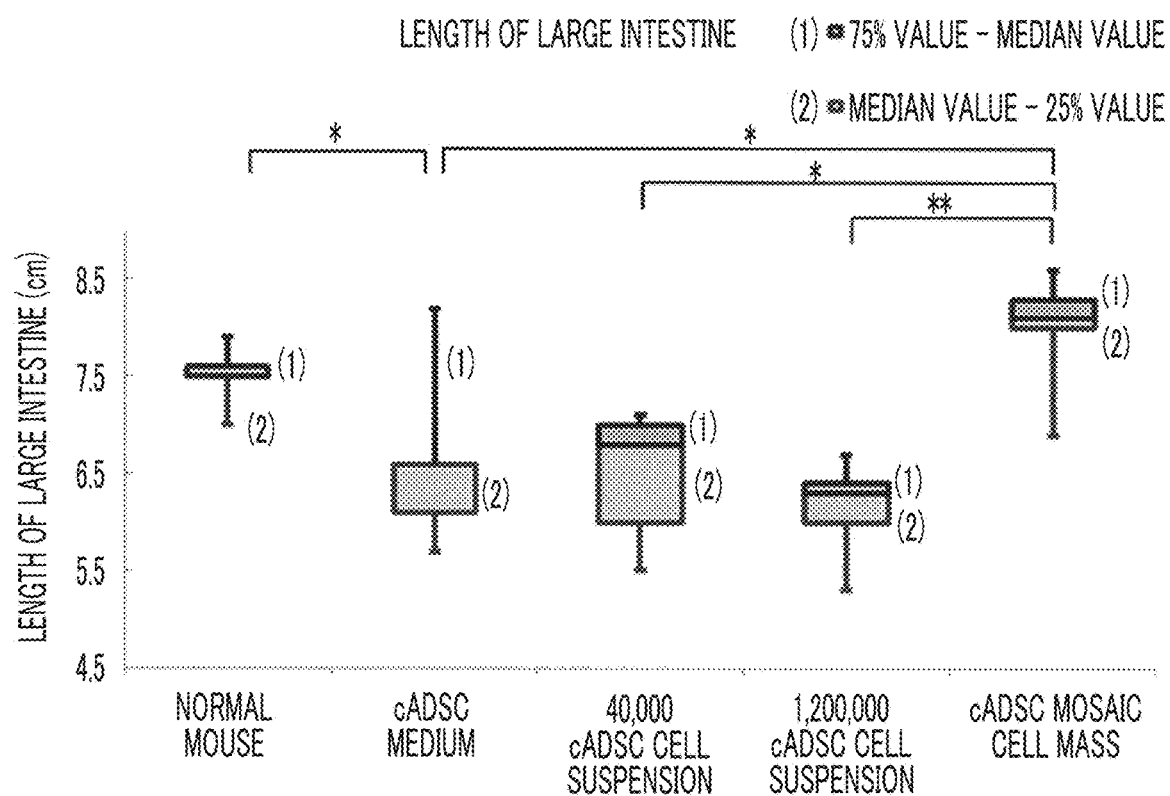
FIG. 17 illustrates results obtained by measuring lengths of large intestines of respective mouse groups.

In Example 25 and Comparative Example 10, the lengths of the large intestines of the respective mouse groups are presented in FIG. 17 as a box plot diagram (in the figure, *: $P<0.05$, **: $P<0.01$ (t test)). As presented in FIG. 17, it was presented that the lengths of the large intestines of the cADSC medium mouse group were significantly shorter than that in the normal mouse group.

In Example 25, the lengths of the large intestines of the cADSC mosaic cell mass mouse group were significantly longer than that of the cADSC medium mouse group which was the comparative example. Accordingly, it was recognized that the cADSC mosaic cell mass improved the short intestinal transformation of the large intestine of the 3.0 mass % DSS colitis model mouse.

Meanwhile, in Comparative Example 10, the length of the large intestine of the cADSC cell suspension mouse group was not different from that of the cADSC medium mouse group which was the comparative example. Accordingly, it was recognized that the cADSC cell suspension did not improve the short intestinal transformation of the large intestine of the 3.0 mass % DSS colitis model mouse.

As the median value of the lengths of the large intestines of the respective mouse groups, the normal mouse group had 7.50 cm, the cADSC medium mouse group had 6.64 cm, the 40,000 cADSC cell suspension mouse group had 6.48 cm, 1,200,000 cADSC cell suspension mouse group had 6.14 cm, and the cADSC mosaic cell mass mouse group had 7.98 cm.

Collectively presenting the evaluation results of the lengths of the large intestines, it was recognized that the cADSC mosaic cell mass had an effect of improving the short intestinal transformation of the 3.0 mass % DSS colitis model mouse. Meanwhile, it was not recognized that the cADSC cell suspension had an effect of improving the short intestinal transformation of the 3.0 mass % DSS colitis model mouse.

From the results of the body weights and the lengths of the large intestines, an inflammation improvement effect on the 3.0 mass % DSS colitis model mouse by the cADSC mosaic cell mass was recognized.

[SEQUENCE LISTING] International Application 17F00633 Trophic Factor Releasing Agent and JP 17022500 20170619—001905520517012909 58 Normal 20170619-143003201706131106359070_P1AP101_17_2.app Based on International Patent Cooperation Treaty

What is claimed is:

1. A method of treating inflammatory disease, comprising:
   transplanting a mosaic cell structure comprising biocompatible polymer blocks and cells, and in which the plurality of biocompatible polymer blocks are disposed in gaps between the plurality of cells, and a site of one of the biocompatible polymer blocks is 20 μm to 200 μm, to a subject in need of treatment of the inflammatory disease, wherein the biocompatible polymer blocks comprise a biocompatible polymer, wherein the biocompatible polymer comprises a recombinant polypeptide, and
   releasing trophic factors from the mosaic cell structure, wherein the trophic factors released by the mosaic cell structure comprise TSG-6.

2. The method of treating inflammatory disease according to claim 1, wherein a size of one of the biocompatible polymer blocks is 50 μm to 120 μm.

3. The method of treating inflammatory disease according to claim 1, wherein, in the biocompatible polymer block, the biocompatible polymer is cross-linked by heat, ultraviolet rays, or an enzyme.

4. The method of treating inflammatory disease according to claim 1, wherein the cell structure includes 0.0000001 μg to 1 μg of biocompatible polymer blocks per cell.

5. The method of treating inflammatory disease according to claim 1, wherein the mesenchymal stem cell is an adipose derived mesenchymal stem cell or a bone marrow derived mesenchymal stem cell.

6. The method of treating inflammatory disease according to claim 1, wherein a biocompatible polymer is gelatin, collagen, atelocollagen, elastin, fibronectin, pronectin, laminin, tenascin, fibrin, fibroin, entactin, or thrombospondin.

7. The method of treating inflammatory disease according to claim 1, wherein the biocompatible polymer is recombinant gelatin.

8. The method of treating inflammatory disease according to claim 7, wherein the recombinant gelatin is:
   a peptide having the amino acid sequence described in SEQ ID No: 1; or
   a peptide having 80% or more sequence identity with the amino acid sequence of SEQ ID NO: 1, and has biocompatibility.

9. The method of treating inflammatory disease according to claim 5, wherein the mesenchymal stem cell is a human or dog derived mesenchymal stem cell.

10. The method of claim 1, wherein the inflammatory disease is inflammatory bowel disease.

11. A method for treating inflammatory disease, comprising:
    administering a mosaic cell structure comprising biocompatible polymer Hocks and cells to a subject in need of treatment of the inflammatory disease, thereby releasing TSG-6 from the cells of the mosaic cell structure,
    wherein the biocompatible polymer blocks are disposed in gaps between the cells,
    wherein a size of one of the biocompatible polymer blocks is 20 μm to 200 μm, and
    wherein the biocompatible polymer blocks comprise a biocompatible polymer, wherein the biocompatible polymer comprises a recombinant polypeptide.

12. The method of claim 11, wherein the biocompatible polymer is gelatin, collagen, atelocollagen, elastin, fibronectin, pronectin, laminin, tenascin, fibrin, fibroin, entactin, or thrombospondin.

13. The method of treating inflammatory disease according to claim 1, wherein a release amount of the trophic factor is increased.

14. The method of treating inflammatory disease according to claim 1, wherein a ratio of a production release amount of the trophic factor in a cell mass to a production release amount of the trophic factor in a mosaic cell structure is 1.4 times or more.

15. The method of treating inflammatory disease according to claim 1, wherein under TNF-a stimulation, a release amount of TSG-6 of the mosaic cell structure was greater than that of the cell mass by 3.1 times or more.

* * * * *